US010688217B2

(12) United States Patent
Hanson et al.

(10) Patent No.: US 10,688,217 B2
(45) Date of Patent: *Jun. 23, 2020

(54) AMINE-FUNCTIONALIZED POLYMERIC COMPOSITIONS FOR MEDICAL DEVICES

(71) Applicant: KCI Licensing, Inc., San Antonio, TX (US)

(72) Inventors: Douglas Philip Hanson, San Antonio, TX (US); James Courage, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 237 days.

This patent is subject to a terminal disclaimer.

(21) Appl. No.: 15/830,528

(22) Filed: Dec. 4, 2017

(65) Prior Publication Data

US 2018/0085489 A1    Mar. 29, 2018

Related U.S. Application Data

(63) Continuation of application No. 15/491,228, filed on Apr. 19, 2017, now Pat. No. 9,861,723, which is a
(Continued)

(51) Int. Cl.
*A61L 26/00* (2006.01)
*A61K 47/34* (2017.01)
(Continued)

(52) U.S. Cl.
CPC .... *A61L 26/0066* (2013.01); *A61F 13/00017* (2013.01); *A61F 13/00063* (2013.01); *A61F 13/00068* (2013.01); *A61K 38/4873* (2013.01); *A61K 47/34* (2013.01); *A61K 47/55* (2017.08); *A61K 47/59* (2017.08); *A61K 47/60* (2017.08);
(Continued)

(58) Field of Classification Search
None
See application file for complete search history.

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

European Examination Report for corresponding Application No. 137858072, dated Oct. 4, 2018.
(Continued)

*Primary Examiner* — Aradhana Sasan

(57) ABSTRACT

The present disclosure provides amine-modified polymer foams, which may be used for wound dressing materials. For example, the modified materials can include a covalently attached molecule comprising free amine groups. Such amine groups can be used, for instance, to conjugate biologically active polypeptides and/or linkers. Methods for using modified polymers are also provided.

22 Claims, 7 Drawing Sheets

Related U.S. Application Data continuation of application No. 14/438,565, filed as application No. PCT/US2013/066671 on Oct. 24, 2013, now Pat. No. 9,657,132.

(60) Provisional application No. 61/718,131, filed on Oct. 24, 2012.

(51) Int. Cl.

| | | |
|---|---|---|
| A61L 15/26 | (2006.01) | |
| A61L 15/42 | (2006.01) | |
| C08G 18/40 | (2006.01) | |
| A61L 15/38 | (2006.01) | |
| A61K 38/48 | (2006.01) | |
| A61K 47/59 | (2017.01) | |
| A61K 47/55 | (2017.01) | |
| A61K 47/60 | (2017.01) | |
| A61L 15/32 | (2006.01) | |
| A61L 15/44 | (2006.01) | |
| C08G 18/08 | (2006.01) | |
| C08G 18/64 | (2006.01) | |
| C08G 18/76 | (2006.01) | |
| C08G 18/32 | (2006.01) | |
| C08G 18/83 | (2006.01) | |
| C08G 18/84 | (2006.01) | |
| C08J 9/36 | (2006.01) | |
| A61F 13/00 | (2006.01) | |
| C08J 9/00 | (2006.01) | |
| C08G 101/00 | (2006.01) | |
| A61K 9/12 | (2006.01) | |

(52) U.S. Cl.

CPC .............. *A61L 15/26* (2013.01); *A61L 15/32* (2013.01); *A61L 15/38* (2013.01); *A61L 15/425* (2013.01); *A61L 15/44* (2013.01); *A61L 26/0085* (2013.01); *C08G 18/14* (2013.01); *C08G 18/3293* (2013.01); *C08G 18/40* (2013.01); *C08G 18/6415* (2013.01); *C08G 18/7621* (2013.01); *C08G 18/833* (2013.01); *C08G 18/84* (2013.01); *C08J 9/00* (2013.01); *C08J 9/36* (2013.01); *C12Y 304/22004* (2013.01); *A61F 2013/0017* (2013.01); *A61K 9/12* (2013.01); *A61L 2300/254* (2013.01); *A61L 2300/404* (2013.01); *A61L 2300/406* (2013.01); *C08G 2101/0083* (2013.01); *C08J 2205/05* (2013.01); *C08J 2207/10* (2013.01); *C08J 2375/12* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,237,229 A | 12/1980 | Hartdegen et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |

(56) References Cited

U.S. PATENT DOCUMENTS

| | | | |
|---|---|---|---|
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 9,657,132 | B2 * | 5/2017 | Hanson .......... A61K 47/34 |
| 9,861,723 | B2 * | 1/2018 | Hanson .......... A61K 47/34 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2014/0163491 | A1 | 6/2014 | Schuessler et al. |
| 2015/0080788 | A1 | 3/2015 | Blott et al. |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| EP | 1935913 A1 | 6/2008 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-2009033088 A1 * | 3/2009 | .......... A61L 27/18 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Phililadelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic

(56) References Cited

OTHER PUBLICATIONS

Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, "Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N. a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

\* cited by examiner

AMINE-FUNCTIONALIZED POLYMERIC COMPOSITIONS FOR MEDICAL DEVICES

CROSS-REFERENCE TO RELATED APPLICATION

This application is a continuation of U.S. application Ser. No. 15/491,228, filed Apr. 19, 2017; which is a continuation of U.S. application Ser. No. 14/438,565, filed Apr. 24, 2015; which is a National Stage of International Application No. PCT/US2013/066671, filed Oct. 24, 2013; which claims priority to U.S. Provisional Application No. 61/718,131, filed Oct. 24, 2012, the disclosures of which are hereby incorporated by reference in their entirety.

FIELD

The present disclosure relates generally to functionalized polymeric material compositions, healing of wounds and wound-treatment therapies. More particularly, but not by way of limitation, the present disclosure relates to modified materials, for example, amine-modified polyurethane foams for use in binding biologically active components.

BACKGROUND INFORMATION

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. One of the major clinical benefits of negative pressure wound therapy is its ability to effectively eliminate wound exudate, thereby reducing edema and allowing tissue decompression. However, in these processes the foams used for application of negative pressure therapy are typically biologically inert. In certain aspects it may be beneficial to bind endogenous compounds at the wound site or to provide biologically active compounds as a part of the foam. Improved foam materials with the ability to deliver and/or capture biologically active components would therefore be desirable.

SUMMARY

The present disclosure provides novel polymeric materials, such as polymeric foams including amine-modified polymers, which may be used to construct medical devices, coat medical devices, or as wound dressing materials. Such modified polymers can, in some aspects, be used to bind biologically active components or agents, such as polypeptides, enzymes, or antimicrobials to the device.

Described herein are functionalized materials comprising amine-functionalized polymers. Described herein are also functionalized foams comprising amine-functionalized polymers. Polymers that may be functionalized with an amine group to covalently link to one or more biologically active components or agents include but are not limited to hydrophobic or hydrophilic polyurethanes, crosslinked and/or uncrosslinked polyolefins, polyester, polyols, ethylene vinyl acetate (EVA), elastomers such as acrylonitrile butadiene (NBR), polychloroprene (PCP or CR), ethylene propylene rubber (EPR & EPDM), poloxamers, polyvinyl alcohols, polystyrenes, silicones, and/or fluoro carbon polymers or a combination thereof. The polymer may be polyurethane. The functionalized foam may be a polyurethane-based foam.

In one embodiment, the amine-functionalized foam may comprise a polymer, such as polyurethane, functionalized with: bifunctional branched or non-branched hydroxyl-PEG-amine compounds ranging from 1 kDa to 60 kDa, bifunctional branched or non-branched amine-PEG-amine compounds ranging from 1 kDa to 60 kDa, bifunctional branched or non-branched HOOC-PEG-amine compounds ranging from 1 kDa to 60 kDa, bifunctional branched or non-branched thiol-PEG-amine compounds ranging from 1 kDa to 60 kDa, bifunctional branched or non-branched hydroxyl-polyol-amine compounds ranging from 1 kDa to 60 kDa, bifunctional branched or non-branched amine-polyol-amine compounds ranging from 1 kDa to 60 kDa, bifunctional branched or non-branched HOOC-polyol-amine compounds ranging from 1 kDa to 60 kDa, bifunctional branched or non-branched thiol-polyol-amine compounds ranging from 1 kDa to 60 kDa, 2-(Triethoxysilylpropoxy)ethoxysulfolane, Trimethylsilylmethyltrifluoro methane sulfonate, Trimethylsilylpropanesulfonic acid, Trimethyl silylmethanesulfonate, Trimethylsilyl isocyanate, N-(Trimethoxysilylpropyl) isothioronium chloride, 2-(3-Trimethoxysilylpropylthio) thiophene, 2-(Trimethylsilyl) phenyltrifluoromethanesulfonate, Trimethylsilylchlorosulfonate, 3-(Trihydroxysilyl)-1-Propanesulfonic acid, Trimethylsilylperfluoro-1-butanesulfonate, Trimethylsilyltrifluoromethanesulfonate, O-(2-Carboxyethyl)-O'-(2-mercaptoethyl)heptaethylene glycol, or an aminoglycoside. The aminoglycoside may be amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisiomycin, streptomycin, tobramycin, and verdamicin, or a combination thereof. In other embodiments, the functionalized wound dressings provided herein comprise a polyurethane-based polymer foam comprising an aminoglycoside of formula (I):

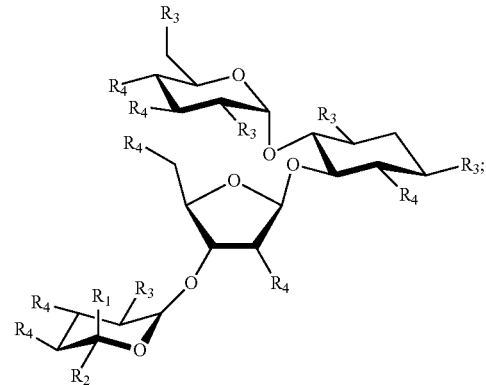

formula (I)

wherein
$R_1$ is H or $CH_2R_3$;
$R_2$ is H or $CH_2R_3$;
$R_3$ is, each independently, $NH_2$, an amide linkage to a biologically active component or agent, an amide linkage to an adapter, or an amide linkage to one of the crosslinkers selected from Table 1; and $R_4$ is, each independently, OH, or a carbamate linkage to the polyurethane-based polymer foam.

In more specific embodiments at least 1 of the $R_4$ positions is each a carbamate linkage to the polyurethane-based polymer foam. The polyurethane-based polymer foam may comprise a plurality of aminoglycosides of formula (I). In specific embodiments, the aminoglycosides may be present in the wound dressing at a ratio of from about 1 to about 40 parts per hundred of the polyurethane. The biologically active component or agent may be a therapeutic agent. The therapeutic agent may be a polypeptide.

In some specific embodiments, at least one of the $R_3$ positions is an amide linkage to a polypeptide. The $R_3$ positions can also comprise an amide linkage to one of the adapters selected from Table 1. Sometimes in these embodiments, the adapter is further attached to a polypeptide, which in non-limiting examples may comprise a thioether linkage. Further, the adapter can be an EMCS-derived adapter or a sulfo-EMCS-derived adapter. The polypeptide molecules may be an enzyme, a growth factor, chemokine, cytokine or a polypeptide that binds to a growth factor, chemokine, or cytokine. The enzyme may be a debridement enzyme. Examples of debridement enzymes include but are not limited bromelain, papain, trypsin, and collagenase. Debridement enzymes may be obtained from various sources, such as mammals or plants. As an example, bromelain may be obtained from pineapple.

In some cases, the polyurethane-based polymer foam is a reticulated open-celled foam. Further, the polyurethane-based polymer foam may comprise one or more additional copolymers such as but not limited to polyvinyl alcohol, polypropylene, polystyrene, polyols, poloxamer, or a combination of one or more of these. The polyurethane-based polymer, in addition to the aminoglycoside, may comprise one or more additional copolymers.

Provided herein are methods for treating a wound comprising contacting a wound site with a functionalized wound dressing as described above. The functionalized wound dressing may be used with negative pressure wound therapy. The method may also involve applying an instillation solution with negative pressure wound therapy. Also provided are methods of using the wound dressing for debridement, biofilm mitigation, and wound healing. As an example, an enzyme for debridement, biofilm mitigation, and/or wound healing may be covalently attached to the functionalized wound dressing to create a multifunctional wound dressing.

Described herein are functionalized material and foam comprising a polymer copolymerized with a amine-polyol or amine-polyethylene glycol (PEG). The functionalized material or foam may be covalently attached with an adapter and/or a crosslinker. The functionalized material or foam may also be covalently attached with a crosslinker through the adapter on the material or foam. The biologically active agent may be attached to the functionalized material or foam through the crosslinker.

Further, some embodiments relate to methods of producing a wound dressing, comprising copolymerizing a diisocyanate and an aminoglycoside. Specific embodiments of these methods may comprise copolymerizing a diisocyanate, an aminoglycoside, and a polyol. In such cases, the aminoglycoside copolymer can be any useful aminoglycoside, including but not limited to neomycin, amikacin, arbekacin, gentamicin, kanamycin, netilmicin, paromomycin, rhodostreptomycin, streptomycin, tobramycin, framycetin or apramycin.

The materials described herein comprise a polyurethane-based material, sheet, solid or semi-solid membrane, permeable or semi-permeable membrane, interfacial layer. The polyurethane-based material may also be used as a coating for beads, catheter, stent, or other devices

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 7A shows uncoated amine-functionalized foam with smooth struts and surfaces. FIG. 7B shows the amine-functionalized foam with covalently bound enzyme matrices (arrows).

DESCRIPTION OF ILLUSTRATIVE EMBODIMENTS

Figure 4:
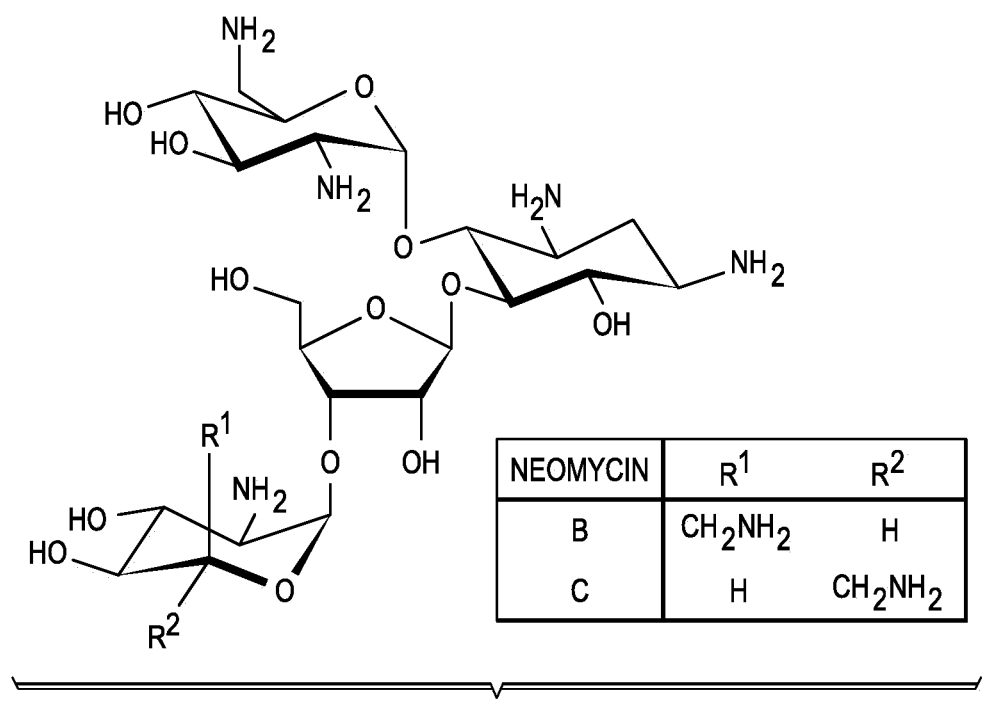
FIG. 4 depicts the structure of neomycin. Neomycin contains —OH groups, that can be used as a polyol in the synthesis of polyurethane. Meanwhile, the —NH$_2$ groups remain unreacted during polyurethane synthesis, leaving the primary amines accessible for further chemical reactions.

Provided herein are amine-functionalized foams, which may be used for wound dressings. Various polymers may be modified with an amine group to become an amine-functionalized foam for use as a wound dressing. Examples of such polymers include but are not limited polyurethane. In certain embodiments modified foams are provided that comprise an amine functionalization of polyurethane. Such amine functionalizations, provide for the covalent binding of various biologically active components to the foams. In some aspects, foams modified to include an amine moiety can be used to link molecules (e.g., therapeutic agents such as peptides or polypeptide) that facilitate the capture of biomolecules, drug/antimicrobial/nanoparticle delivery, detection/diagnostics, regulation of the wound environment, and possibly biodegradation. For example, in some aspects, an amine functionalized foam can be produced by copolymerization of an aminoglycoside (i.e., molecules comprising several amino sugars connected by glycoside bonds), such as neomycin (FIG. 4), with a diisocyanate (e.g., toluene diisocyanate). The resulting amine-modified foams include free amine positions that can be further modified for linkage to biologically active components or agents. An example of such an amine moiety for functionalization of foams is neomycin (2S,3S,4S,5R)-5-amino-2-(aminomethyl)-6-((2R,3S,4R,5S)-5-(((1R,2R,5R,6R)-3,5-diamino-2-((2R,3S,4R,5S)-3-amino-6-(aminomethyl)-4,5-dihydroxytetrahydro-2H-pyran-2-yloxy)-6-hydroxycyclohexyloxy)-4-hydroxy-2-(hydroxymethyl)tetrahydrofuran-3-yloxy)tetrahydro-2H-pyran-3,4-diol, hereforth referred to as "aminoglycoside", and structurally depicted as:

formula (I)

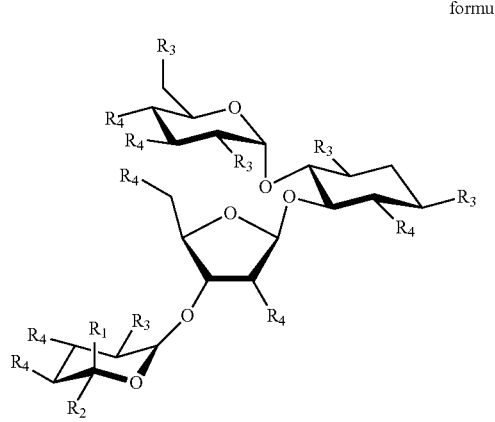

where

R₁ is H or CH₂R₃;

R₂ is H or CH₂R₃;

R₃ represents free NH₂ positions or positions that can be occupied by a biologically active component, such as a polypeptide, attached by an adapter or crosslinker.

R₄ represents OH positions, some of which, can provide a carbamate linkage to the polyurethane-based polymer foam.

In certain embodiments, wound dressings comprising a functionalized foam are provided. The foam may comprise polyurethane foam functionalized with an aminoglycoside having a free amine position for linkage to biologically active component or agent. Examples of aminoglycoside include but are not limited to amikacin, apramycin, arbekacin, astromicin, bekanamycin, dibekacin, framycetin, gentamicin, hygromycin B, isepamicin, kanamycin, neomycin, netilmicin, paromomycin, rhodostreptomycin, ribostamycin, sisiomycin, streptomycin, tobramycin, verdamicin, and salts thereof. An example of a salt of an aminoglycoside is paromomycin sulfate.

Figure 5:
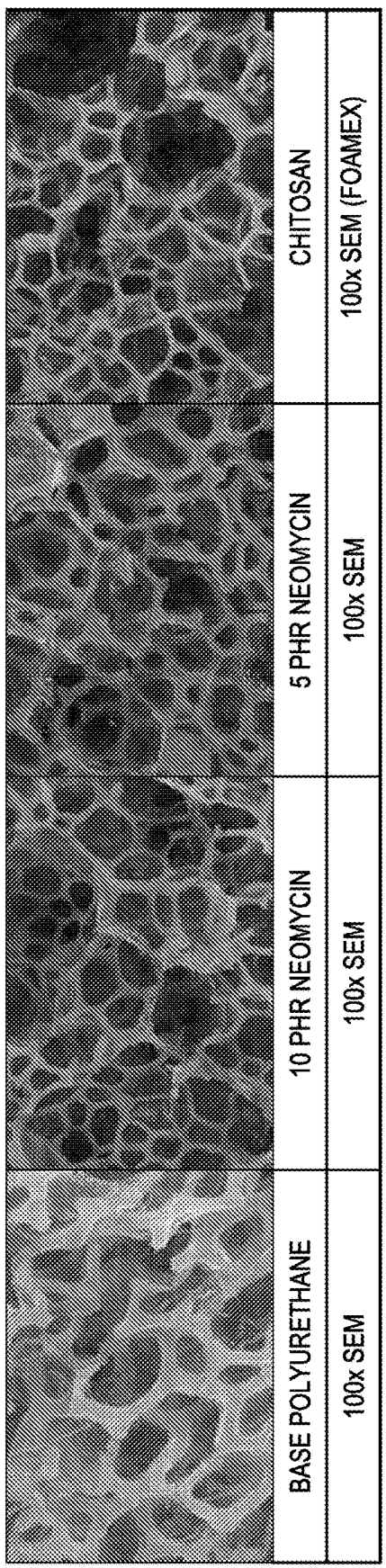
FIG. 5 depicts 100× scanning electron microscope (SEM) images of ROCF in neomycin foam. SEM images illustrate the presence of ROCF in the 5 phr and 10 phr foams.
Figure 6:
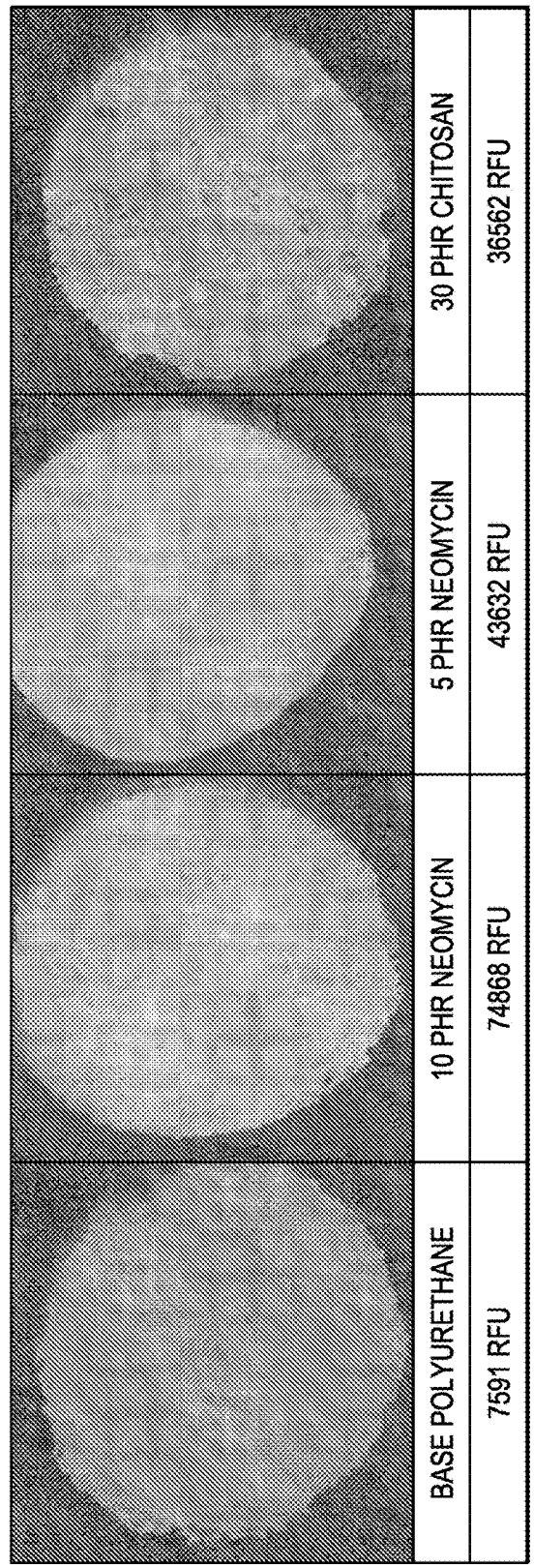
FIG. 6 depicts the results of studies assessing of amine reactivity of neomycin-modified foams. Fluorescence was quantified for each treatment condition and is indicated in the bottom panel.

Studies detailed below confirm that such amine-modified foams were robust and retained a reticulated open cell structure (FIG. 5). Importantly, the foams were able to withstand 40 Kgy gamma sterilization, a crucial feature for any wound dressing material. These studies also confirmed, by dye-binding studies, that free amine positions were present through-out the foams (FIG. 6). Thus, aminoglycosides such as, neomycin polymerized well with isocyanate chemistry acting effectively as a polyol in the reaction. When the reaction occurs, the —OH groups polymerize with isocyanate, but the primary amine groups (NH₂) remain partially unreacted for further chemical reactions.

Free amine positions on the modified foams detailed herein can be attached to biologically active molecules by a variety of well known chemistries. For example, any of the adapter molecules provided in Table 1 can be used for covalent attachment of biologically active components or agents, such as polypeptides. The four main chemistries being amine, sulfhydryl, non-selective and carboxyl. Finally, amine-functionalized foams can be used for direct conjugation that does not require a crosslinker, such as the bond formed between a primary amine group and a carboxylic acid in a peptide bond.

The amine-modified foams of the embodiments therefore provide platforms for capture of biomolecules; drug/antimicrobial/nanoparticle delivery; detection/diagnostics (e.g., of bound components); regulation of the wound environment; and/or biodegradation/reabsorption.

A. Definitions

When used in the context of a chemical group, "hydrogen" means —H; "hydroxy" means —OH; "oxo" means=O; "halo" means independently —F, —Cl, —Br or —I; "amino" means —NH₂ (see below for definitions of groups containing the term amino, e.g., alkylamino); "hydroxyamino" means —NHOH; "nitro" means —NO₂; imino means=NH (see below for definitions of groups containing the term imino, e.g., alkylimino); "cyano" means —CN; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; "thio" means=S; "thioether" means —S—; "sulfonamido" means —NHS(O)₂— (see below for definitions of groups containing the term sulfonamido, e.g., alkylsulfonamido); "sulfonyl" means —S(O)₂— (see below for definitions of groups containing the term sulfonyl, e.g., alkylsulfonyl); and "sulfinyl" means —S(O)— (see below for definitions of groups containing the term sulfinyl, e.g., alkylsulfinyl).

The symbol "—" means a single bond, "═" means a double bond, and "≡" means triple bond. The symbol "----" represents an optional bond, which if present is either single or double. The symbol "⚌" represents a single bond or a double bond. Thus, for example, the structure

includes the structures

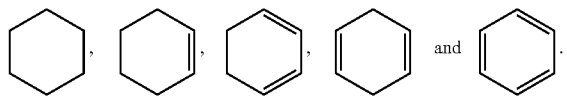

As will be understood by a person of skill in the art, no one such ring atom forms part of more than one double bond. The symbol "〜", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂▬" means a single bond where the group attached to the thick end of the wedge is "out of the page." The symbol "⫶⫶⫶" means a single bond where the group attached to the thick end of the wedge is "into the page". The symbol "⁓" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

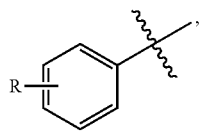

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

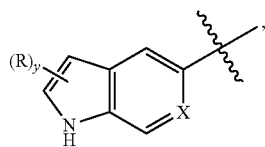

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(Cn≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neopentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) CH$_3$, —N(CH$_3$)$_2$, —C(O)NH$_2$ or —OC(O)CH$_3$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "fluoroalkyl" is a subset of substituted alkyl, in which one or more hydrogen has been substituted with a fluoro group and no other atoms aside from carbon, hydrogen and fluorine are present. The groups, —CH₂F, —CF₃, and —CH₂CF₃ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH₂ (vinyl), —CH=CHCH₃, —CH=CHCH₂CH₃, —CH₂CH=CH₂ (allyl), —CH₂CH=CHCH₃, and —CH=CH—C₆H₅. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH₃)CH₂—, —CH=CHCH₂—, and

are non-limiting examples of alkenediyl groups. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂ or —OC(O)CH₃. The groups, —CH=CHF, —CH=CHCl and —CH=CHBr, are non-limiting examples of substituted alkenyl groups. An "alkene" refers to the compound H—R, wherein R is alkenyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

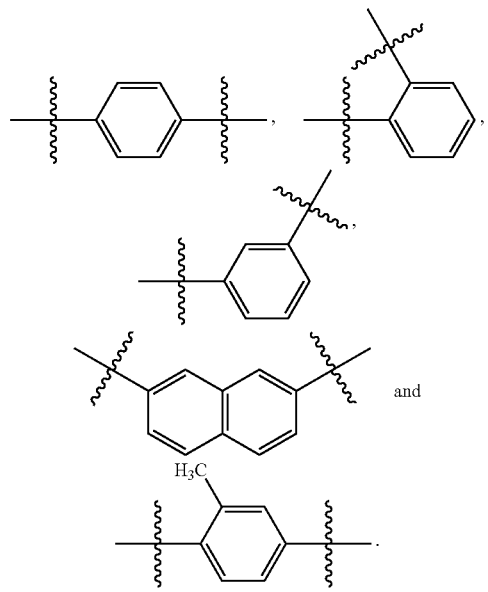

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂ or —OC(O)CH₃. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂ or —OC(O)CH₃. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl, indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of heteroarenediyl groups include:

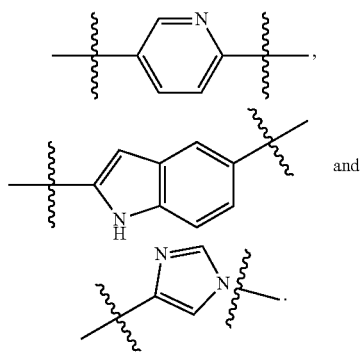

and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups, —C(O)CH$_2$CF$_3$, —CO$_2$H (carboxyl), —CO$_2$CH$_3$ (methyl carboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Similarly, the term "alkylthio" when used without the "substituted" modifier refers to the group —SR, in which R is an alkyl, as that term is defined above. The term "alkoxydiyl" when used without the "substituted" modifier refers to the divalent group —O-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$ or —OC(O)CH$_3$.

The term "glycoside" refers to a compound in which a sugar group is bound to a non-carbohydrate moiety. Typically the sugar group (glycone) is bonded through its anomeric carbon to another group (aglycone) via a glycosidic bond that has an oxygen, nitrogen or sulfur atom as a linker.

A "simple sugar" is the basic structural unit of carbohydrates, which cannot be readily hydrolyzed into simpler units. The elementary formula of a simple monosaccharide is $C_nH_{2n}O_n$, where the integer n is at least 3 and rarely greater than 7. Simple monosacharides may be named generically according on the number of carbon atoms n: trioses, tetroses, pentoses, hexoses, etc. Simple sugars may be open chain (acyclic), cyclic or mixtures thereof. In these cyclic forms, the ring usually has 5 or 6 atoms. These forms are called furanoses and pyranoses, respectively—by analogy with furan and pyran. Simple sugars may be further classified into aldoses, those with a carbonyl group at the end of the chain in the acyclic form, and ketoses, those in which the carbonyl group is not at the end of the chain. Non-limiting examples of aldoses include: glycolaldehyde, glyceraldehydes, erythrose, threose, ribose, arabinose, xylose, lyxose, allose, altrose, glucose, mannose, gulose, idose, galactose and talose. Non-limiting examples of aldoses include: dihydroxyacetone, erythrulose, ribulose, xylulose, fructose, psicose, sorbose and tagatose. The 'D-' and 'L-' prefixes may be used to distinguish two particular stereoisomers which are mirror-images of each other. The term simple sugar also covers O-acetyl derivatives thereof.

An "amino sugar" or "aminoglycoside" refers to a derivative of a sugar, deoxy sugar, sugar acid or sugar alcohol, where one or more hydroxy group(s) has been replace with one more amino group(s). An "amino sugar" refers to a derivative of a simple sugar, simply deoxy sugar, simply sugar acid or sugar alcohol, where one or more hydroxy group(s) has been replaced with one more amino group(s). These terms also cover N- and O-acetyl derivatives thereof. Non-limiting examples include N-acetylglucosamine, galactosamine, glucosamine and sialic acid.

The term "deoxy sugar" refers to a sugar derivative where one of the hydroxy groups of a carbohydrate has been replaced with a hydrogen atom. A "simple deoxy sugar" is a deoxy sugar derived from a simple sugar, as defined herein. These terms also cover O-acetyl derivatives thereof. Non-limiting examples of simple deoxy sugars are deoxyribose (based upon ribose), fucose, and rhamnose.

The term "sugar acid" refers to a sugar derivative where an aldehyde functional group or one or more hydroxy functional groups has been oxidized to a carboxyl group. Aldonic acids are those in which the aldehyde functional group of an aldose has been oxidized. Ulosonic acids are those in which the first hydroxyl group of a 2-ketose has been oxidized creating an α-ketoacid. Uronic acids are those in which the terminal hydroxyl group of an aldose or ketose has been oxidized. Aldaric acids are those in which both ends of an aldose have been oxidized. Non-limiting aldonic acids include glyceric acid (3C), xylonic acid (5C), gluconic acid (6C), and ascorbic acid (6C, unsaturated lactone). Non-limiting examples of ulosonic acids include neuraminic acid (5-amino-3,5-dideoxy-D-glycero-D-galacto-non-2-ulosonic acid) and ketodeoxyoctulosonic acid (KDO or 3-deoxy-D-manno-oct-2-ulosonic acid). Non-limiting examples of uronic acids include glucuronic acid (6C), galacturonic acid (6C), and iduronic acid (6C). Non-limiting example of aldaric acids include tartaric acid (4C), meso-galactaric acid (mucic acid) (6C), and D-glucaric acid (saccharic acid) (6C). A "simple sugar acid" is a sugar acid derived from a simple sugar. These terms also cover O-acetyl derivatives thereof.

The term "sugar alcohol" refers to a sugar derivative whose carbonyl group (aldehyde or ketone, reducing sugar) has been reduced to a primary or secondary hydroxyl group. Non-limiting examples of sugar alcohols include: glycol (2-carbon), glycerol (3-carbon), erythritol (4-carbon), threitol (4-carbon), arabitol (5-carbon), xylitol (5-carbon), ribitol (5-carbon), mannitol (6-carbon), sorbitol (6-carbon), dulcitol (6-carbon), iditol (6-carbon), isomalt (12-carbon), maltitol (12-carbon), lactitol (12-carbon) or polyglycitol. A "simple sugar alcohol" is a sugar alcohol derived from a simple sugar. These terms also cover O-acetyl derivatives thereof.

As used herein, the term "monosaccharide group" refers to a monovalent carbohydrate group, with a carbon atom as the point of attachment. The term covers the groups resulting from removal of a hydroxyl radical from a simple sugar (e.g., glucose), simple deoxy sugar (e.g., fucose), simple sugar acid (e.g., gluconic acid), simple sugar alcohol (e.g., xylitol) or simple amino sugar (e.g., glucosamine). Typically the monosaccharide group is bonded through its anomeric carbon to another group (aglycone) via oxygen atom linker. In some cases the linker may be a nitrogen or sulfur atom.

A "disaccharide group" is a monovalent carbohydrate group consisting of two monosaccharide groups, wherein the second monosaccharide group replaces a hydrogen on a hydroxy group of the first monosaccharide group. Non-limiting examples of disaccharide groups include those derived from sucrose, lactulose, lactose, maltose trehalose and cellobiose.

A "trisaccharide group" is a monovalent carbohydrate group consisting of three monosaccharide groups, wherein the second monosaccharide group replaces a hydrogen on a hydroxy group of the first monosaccharide group and the third monosaccharide group replaces a hydrogen on a hydroxy group of either the first or the second monosaccharide groups.

An oligosaccharide is a monovalent carbohydrate group consisting of three to ten, preferably three to six monosaccharide groups, wherein the second monosaccharide replaces a hydrogen on a hydroxy group of the first monosaccharide, the third monosaccharide replaces a hydrogen on a hydroxy group of either the first or the second monosaccharide groups, and subsequent monosaccharide groups replace hydrogens on any previously joined monosaccharide groups, thus forming either a linear or branched structure.

The term "silyl" when used without the "substituted" modifier refers to the group —$SiR_3$, where each R is independently hydrogen or unsubstituted alkyl, as that group is defined above. The term "substituted silyl" refers to the group, —$SiR_3$, wherein at least one of the R groups and as many as all of the R groups, is independently a substituted alkyl or —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$N(CH_3)_2$, —$C(O)NH_2$ or —$OC(O)CH_3$. Any remaining R groups of the substituted silyl group are independently hydrogen or unsubstituted alkyl. The term "silylated" or "silanated" indicates that a given compound has been derivatized to contain a silyl and/or substituted silyl group. The abbreviation "-Sil" refers to silyl and/or substituted silyl groups.

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises a wound insert and a drape, the wound dressing includes the specified elements but is not limited to having only those elements. For example, such a wound dressing could also include a connection pad configured to be coupled to a wound-treatment apparatus.

The term "effective," as that term is used in the specification and/or claims, means adequate to accomplish a desired, expected, or intended result.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"PBS" is phosphate buffered saline; "phr" is parts per hundred resin; "OPA" is ortho-pthaldialdehyde; "RT" is room temperature.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "polymer" includes "copolymers."

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —$[CH_2CH_2]_n$—, the repeat unit is —$CH_2CH_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc.

The term "reticulated open cell foam" or ROCF refers to a foam material with a porous structure consisting of an interconnected network of solid struts. The open cells are formed by the reticulation process, which is in turn defined as in the form of a network or having a network of parts. Because all struts are connected, the open cell porosity is also connected creating a continuously porous material. The ROCF can be defined specifically by three independent properties; pore size, relative density, and base material. In some embodiments, ROCF is made from polyurethane.

The above definitions supersede any conflicting definition in any of the reference that is incorporated by reference herein. The fact that certain terms are defined, however, should not be considered as indicative that any term that is undefined is indefinite. Rather, all terms used are believed to describe the embodiments in terms such that one of ordinary skill can appreciate the scope and practice the embodiments.

Further, a device or structure that is configured in a certain way is configured in at least that way, but it can also be configured in other ways than those specifically described.

B. Amine-Modified Materials

In one aspect, described herein, is a covalent system for attaching amine moieties to the foam, for example, the polyurethane-based foam. Such moieties can in turn be used to bind biologically active components. In some case, these components can be used for catching and concentrating specific factors in the wound environment, including factors that trigger a significant biological response, such as proliferation, differentiation, or angiogenesis. This technology may be used, for example, to deliver biomolecules or bioactive compounds to the wound bed. Amine-modified materials provided herein may be used in some embodiments as a system for catching and concentrating specific factors in the wound environment, such as, factors triggering a biological response such as angiogenesis, or to deliver endogenous or exogenous biomolecules or bioactive compounds to the wound bed.

In one aspect, the amine-modified materials and foams provided herein comprise a polymer, such as polyurethane, copolymerized with at least one aminoglycoside, amino sugar, amine-polyethylene glycol (amine-PEG), or amine-polyol molecule. The aminoglycoside, amino sugar, amine-PEG, or amine-polyol is covalently attached to the polymer comprising a free amine group. In some aspects, modified materials further comprise a biologically active component attached to the functional group. It will be further understood that such biologically active molecules can be directly attached to the functional group by way of a crosslinker, or a through a crosslinker, conjugated to an adapter, which is conjugated to the foam. The crosslinker or adapter for linking the biologically active component or agent, such as a therapeutic agent, may be cleavable. A solution, such as an instillation solution, may be employed to cleave the therapeutic agent and deliver the therapeutic agent to the wound site.

The biologically active agent may be covalently attached to the amine-modified foam by any physical or chemical methods including but not limited to methods that involve temperature, pressure, pH, radiation, light, UV light, freeze-drying, and sterilization.

A list of exemplary crosslinkers are provided below in Table 1.

In other embodiments, the biologically active molecule, such as a therapeutic agent, may be covalently attached to the polyurethane-based foam through a crosslinker, covalently attached to an adapter, which is conjugated to the foam. The polyurethane-based foam may not include an aminoglycoside.

Suitable Polymers

Polymers for use with the present embodiments include hydrophobic or hydrophilic polyurethanes, crosslinked and/or uncrosslinked polyolefins, polyols, ethylene vinyl acetate (EVA), elastomers such as acrylonitrile butadiene (NBR), polychloroprene (PCP or CR), ethylene propylene rubber (EPR & EPDM), poloxamers, silicones, fluoro carbon polymers, polyvinyl alcohol, polyester, polypropylene, polystyrene, polyols, poloxamer, or a combination thereof.

The foams described herein may comprise one or more copolymers. For example, in some embodiments, the polymer may be a polyurethane polymer. In other embodiments, the polymer may be a blend of a polyurethane and one or more other copolymers, such as polyvinyl alcohol or polypropylene.

Polyurethanes are reaction polymers. A urethane linkage is produced by reacting an isocyanate group, —N=C=O with a hydroxy group, and polyurethanes are produced by the polyaddition reaction of a polyisocyanate with a diol or a polyol, typically in the presence of a catalyst and other

TABLE 1

Table shows 51 potential crosslinker chemistries that react with primary amines. Several of these crosslinkers are cleavable, and thus they may be used as a vehicle for delivery of molecules into the wound environment if they are coupled with an appropriate solution, for example an instillation solution.

| Target | Features | Specific examples |
|---|---|---|
| Amine-to-amine | NHS esters | DSG; DSS; BS3; TSAT (trifunctional) |
| | NHS esters, PEG spacer | BS(PEG)5; BS(PEG)9 |
| | NHS esters, thiol-cleavable | DSP; DTSSP |
| | NHS esters, misc-cleavable | DST; BSOCOES; EGS; Sulfo-EGS |
| | Imidoesters | DMA; DMP; DMS |
| | Imidoesters, thiol-cleavable | DTBP |
| | Other | DFDNB |
| Amine-to-sulfhydryl | NHS ester/Maleimide | AMAS; BMPS; GMBS and Sulfo-GMBS; MBS and Sulfo-MBS; SMCC and Sulfo-SMCC; EMCS and Sulfo-EMCS; SMPB and Sulfo-SMPB; SMPH; LC-SMCC; Sulfo-KMUS |
| | NHS ester/Maleimide, PEG spacer | SM(PEG)2; SM(PEG)4; SM(PEG)6; SM(PEG)8; SM(PEG)12; SM(PEG)24 |
| | NHS ester/Pyridyldithiol, cleavable | SPDP; LC-SPDP and Sulfo-LC-SPDP; SMPT; Sulfo-LC-SMPT |
| | NHS esters/Haloacetyl | SIA; SBAP; SIAB; Sulfo-SIAB |
| Amine-to-Nonselective | NHS ester/Aryl Azide | NHS-ASA; ANB-NOS; Sulfo-SANPAH |
| | NHS ester/Aryl Azide, cleavable | Sulfo-SAND |
| | NHS ester/Diazirine | SDA and Sulfo-SDA; LC-SDA and Sulfo-LC-SDA |
| | NHS ester/Diazirine, cleavable | SDAD and Sulfo-SDAD |
| Amine-to-Carboxyl | Carbodiimide | DCC; EDC |

In one embodiment, the crosslinker for linking a biologically active molecule to the amine-modified foam may be malondialdehyde, succinaldehyde, pthaldehyde, glutaraldehyde, or glyoxal.

additives. A polyisocyanate is a molecule with two or more isocyanate functional groups, $R—(N=C=O)_n$, wherein $n \geq 2$ and a polyol is a molecule with two or more hydroxyl functional groups, $R'—(OH)_n$, wherein $\geq 2$. The reaction product is a polymer containing the urethane linkage, —RN-HCOOR'—. Polyurethanes may be produced by reacting a liquid isocyanate with a liquid blend of polyols, catalyst, and other additives. The blend of polyols and other additives may also be called a resin or a resin blend. In some aspects, the linker moiety acts in the polymerization reaction as a polyol and is therefore substituted for all or a portion of the polyol used in a polymerization reaction. In some embodiments, resin blend additives may include chain extenders, cross linkers, surfactants, flame retardants, blowing agents, pigments, and/or fillers. The synthesis of breathable or air-permeable, open cell, flexible urethane polymers is taught for example by U.S. Pat. No. 5,686,501, which is incorporated by reference herein in its entirety.

Molecules that contain two isocyanate groups are called diisocyanates. Isocyanates may be classed as aromatic, such as diphenylmethane diisocyanate (MDI), diphenylethane diisocyanate (EDI), or toluene diisocyanate (TDI); or aliphatic, such as hexamethylene diisocyanate (HDI) or isophorone diisocyanate (IPDI). An example of a polymeric isocyanate is polymeric diphenylmethane diisocyanate, which is a blend of molecules with two-, three-, and four- or more isocyanate groups. Isocyanates can be further modified by partially reacting them with a polyol to form a prepolymer. A "quasi-prepolymer" is formed when the stoichiometric ratio of isocyanate to hydroxyl groups is greater than 2:1. A "true prepolymer" is formed when the stoichiometric ratio is equal to 2:1. Important characteristics of isocyanates include their molecular backbone, % NCO content, functionality, and viscosity.

Molecules that contain two hydroxyl groups are called diols. Examples include, ethylene glycol (EG), 1,4-butanediol (BDO), diethylene glycol (DEG). Molecules that contain three hydroxyl groups are called triols. Examples include glycerol. Polyols may themselves be polymers. For example, they may be formed by base-catalyzed addition of propylene oxide (PO), ethylene oxide (EO) onto a hydroxy or amino-containing initiator, or by polyesterification of a di-acid, such as adipic acid, with glycols, such as ethylene glycol or dipropylene glycol (DPG). Polyols extended with PO or EO are typically called polyether polyols. Polyols formed by polyesterification are typically called polyester polyols. The choice of initiator, extender, and molecular weight of the polyol will typically affect its physical state, and the physical properties of the resulting polyurethane. Important characteristics of polyols are their molecular backbone, initiator, molecular weight, % primary hydroxyl groups, functionality, and viscosity.

One attribute of polyurethanes is their ability to be turned into foam. As the reagents react with one another, carbon dioxide gas is created, which fills and expands cells created during the mixing process. Blowing agents may also be used, including certain halocarbons such as HFC-245fa (1,1,1,3,3-pentafluoropropane) and HFC-134a (1,1,1,2-tetrafluoroethane), and hydrocarbons such as n-pentane. In some embodiments, surfactants may be used to modify the characteristics of the polymer during the foaming process.

Though the properties of the polyurethane are typically determined mainly by the choice of polyol, the diisocyanate exerts some influence. For example, the cure rate will generally be influenced by the reactivity of a given functional group and the number of functional isocyanate groups.

Softer, elastic, and more flexible polyurethanes typically result when linear difunctional polyethylene glycol segments, commonly called polyether polyols, are used to create the urethane links. More rigid products typically result if polyfunctional polyols are used, as these create a three-dimensional cross-linked structure which, again, can be in the form of a low-density foam. Control of viscoelastic properties, for example, by modifying the catalysts and polyols used can lead to memory foam, which is much softer at skin temperature than at room temperature.

In some embodiments, the polyurethane foam is formed by the polymerization of isocyanates and polyols, typically toluene diisocyanate and a multi arm polyether polyol. These components may be indexed, such that the isocyanate and hydroxyl group are in a one to one ratio.

Formulations of various PHR (grams of [molecule] Per Hundred grams of polyurethane Resin) of amine-containing molecules, such as neomycin, have been produced and tested. They have been characterized by the amount of surface amine available for bonding by conjugation of the foam with a dye. In both cases the relative fluorescence units RFU were found to be proportional to the primary amine available on the surface of the foam (see FIG. 6).

In some embodiments, the foam including the polyurethane foam may comprise an additional polymer selected from the group consisting of polyvinyl alcohol, polyurethane, polypropylene, polystyrene, polyols, poloxamer, or a combination of one or more of these. Accordingly, the wound dressing described herein may comprise a polymer foam comprising a one or more polymers and an aminoglycoside.

Further Modified Polymer Backbone

In some embodiments, substituted silyl-modified polymers are provided. Examples include those comprising repeat units based on polyurethane, which may be hydrophobic or hydrophilic, crosslinked and/or uncrosslinked polyolefin, polyols, ethylene vinyl acetate (EVA), elastomers such as acrylonitrile butadiene (NBR), polychloroprene (PCP or CR), amine-functionalized polyethylene glycol molecules, ethylene propylene rubber (EPR & EPDM), silicones, and/or fluoro carbon polymers. For example, in some embodiments, an amino sugar-based polyurethane polymers or copolymers may be used. In some embodiments, the substituted silyl groups are attached to the polymer or co-polymer through an oxygen atom. In other embodiments, the substituted silyl groups are attached directly to a carbon atom of the polymer or co-polymer.

Some embodiments provide polymeric materials modified with silane molecules, containing substituted silyl groups. Examples of foam materials can include polyurethane-based foam, which may be hydrophobic or hydrophilic, including, for example an amino sugar-based polyurethane foam material. Other foams that may be suitable include amino sugars, crosslinked and/or uncrosslinked polyolefin's, polyols, ethylene vinyl acetate (EVA), and elastomers such as acrylonitrile butadiene (NBR), polychloroprene (PCP or CR), ethylene propylene rubber (EPR & EPDM), silicones, and fluoro carbon polymers. For example, in some embodiments, a amino sugars-based polyurethane foam may be used. In some embodiments, the substituted silyl groups are attached to the foam through an oxygen atom. In other embodiments, the substituted silyl groups are attached directly to a carbon atom of the foam.

The silylated polyurethane foams disclosed herein may be made by silylating the hydroxy groups on a polymer comprising such groups. As used herein, silylation is the introduction of a substituted silyl group ($R_3Si$—) to a molecule. It involves the replacement of a hydrogen on the compound, e.g., the hydrogen of a hydroxy group, with an substituted silyl group. Without being bound by mechanism, the oxygen atom of the product, may be the same oxygen atom of the hydroxy group reactant. See "How do I apply my Silane?" Gelest Catalog. 2006, pages 19-20, which are incorporated by reference herein in their entirety.

In some embodiments, the N-hydroxysuccinimide ester (NHS ester) on one end of the Sulfo-EMCS molecule can react with free amine groups of a modified polymer. The maleimide group on the other end of the molecule may be used to react, for example, with —SH groups on a peptide aptamer to form stable thioether bonds. In this manner the Sulfo-EMCS may be used to link the peptide to a polymer or copolymer, including a foam.

Furthermore, the peptides used in maleimide-thiol conjugation typically have specially modified C-termini. For example, the C-termini may be "capped" with Cys residues bearing reactive —SH groups to facilitate the conjugation. In a Sulfo-EMCS conjugations, Sulfo-EMCS is typically used in excess, for example, in 50-100× molar excess relative to an organosilane crosslinkers to facilitate the reaction. Such reactions may be carried out, for example, at pH 7.0-7.5 and at room temperature. Such methods may be further modified and optimized using the principles and techniques of organic chemistry as applied by a person skilled in the art. Such principles and techniques are taught, for example, in March's Advanced Organic Chemistry: Reactions, Mechanisms, and Structure (2007), which is also incorporated by reference herein in its entirety. For example, other suitable amine-thiol linkers may be used. These include, for example: SM(PEG)24, SM(PEG)12, SM(PEG)8, SM(PEG)6, SM(PEG)4, Sulfo-LC-SMPT, SM(PEG)2, Sulfo-KMUS, LC-SMCC, LC-SPDP, Sulfo-LC-SPDP, SMPH, Sulfo-SMPB, SMPB, SMPT, STAB, Sulfo-SIAB, EMCS, Sulfo-SMCC, SMCC, MBS, GMBS, Sulfo-GMBS, Sulfo-MBS, SPDP, SBAP, BMPS, AMAS, and SIA.

In some embodiments, the silanes or aminoglycosides and/or amino sugar polymers will be further modified with additional linker or adapter molecules, for example, oligopeptide oligomers or an adapter of Table 1. In some embodiments, the additional linkers are covalently attached to the backbone of the silylated or aminoglycoside and/or amino sugar-modified polymer or copolymer. In other embodiments, the linker is covalently attached to a side chain or side group of the polymer or copolymer. In some embodiments, the additional linker is attached via a functional amine group of a modified-polymer or copolymer, forming a material.

Biologically Active Components or Agents and Modified Polymer Backbone

Described herein are wound dressings having an amine-functionalized material or foam comprising a biologically active component or agent. The biologically active component or agent may be a therapeutic agent for treating a wound. One or more therapeutic agents may be covalently or non-covalently attached to the modified polymer, a polyurethane-based foam. The biologically active agent may be covalently or non-covalently attached to the material or foam through methods that involve temperature, pressure, pH, radiation, light, UV light, freeze-drying, and sterilization.

These agents include, but are not limited to: peptides, ligands, polypeptides, peptide and protein matrices, carbohydrates, lipids, oligonucleotides, antimicrobials, small molecules, nanoparticles, nanobots, aliphatic hydrocarbon chains, surfactants, metals, and alginates, aptamers, or a combination thereof. The wound dressing may be a multifunctional dressing comprising one or more biologically active components or agents. The therapeutic agent may be covalently attached to the modified polymer via a chemical linkage.

Examples of peptides include insulin and insulin-like peptides, quorum sensing inhibitors, defensins, Cathelicidins, synthetic peptides, and peptides that reversibly bind other peptide or protein targets.

Examples of polypeptides include extracellular matrix polypeptides, gelatin, collagen, albumin, whole or partial antibodies, C-1 complement components, cytokines, growth factors, and enzymes. The enzyme may be a protease, a kinase, or a phosphatase obtained from various sources, such as plants or animals. The enzymes may be used for debridement, biofilm mitigation, wound healing, or a combination thereof. Some examples of debridement enzymes include proteases such as bromelain, papain, collagenase, and trypsin. Some examples of enzymes for biofilm mitigation include carboxypeptidase A, clostripain, and D-amino acid oxidase. Some examples of wound healing enzymes include catalases, ligases, isomerases, and hydrolases.

Examples of peptide and protein matrices include denatured and non-denatured protein and peptide matrices. The peptide or protein matrix may comprise peptides, proteins, or enzymes that may be crosslinked with a linking agent. Examples of denatured peptide and protein matrices used in this manner may include but are not limited to denatured albumin and denatured collagen. Non-denatured peptides and proteins used in this manner may include but are not limited to cytokines, growth factors, proteases, and other enzymes.

Examples of carbohydrates include but are not limited to natural or synthetically modified monosaccharides and polysaccharides. Both monosaccharides and polysaccharides may be either human or microbial in nature. The polysaccharide may be a mucopolysaccharide such as a glycosaminoglycan. An example of a glycosaminoglycan is heparin.

Some examples of antimicrobials include quaternary ammonium compounds, povidone-iodine, polyhexanide, antibiotics, and antimicrobial polypeptides. An example of an antimicrobial polypeptide is LL-37.

Examples of small molecules include agonists and antagonists that may promote wound healing. These small molecules may comprise endogenous or exogenous: mineral cofactors such as calcium, sodium, potassium, zinc, and magnesium, provided in their elemental or pharmaceutical salt form; biomolecules such as natural or synthetic regulatory peptides or peptide mimetics; drugs; metabolites of oxidative respiration; and, natural or synthetic neurotransmitters. Examples of small molecule agonists used in this system comprise but are not limited to, epinephrine and norepinephrine. Examples of small molecule antagonists used in this system comprise but are not limited to cyclothiazide and buprenorphine hydrochloride. Examples of aptamers include dendrimers, biotin, and avidin.

In some embodiments, biologically active components or agents, including peptide-based aptamers, may be conjugated to a polymer or copolymer. Such polypeptides also referred to as "capture peptides", can be used to bind protein targets in the wound environment without inhibiting their signaling capabilities or other functions. Such capture peptides may also be used to capture and increase concentrations of biologically active proteins across a wound bed of a patient, for example, to strengthen or activate a targeted biological response. These and other uses are described in greater detail below.

In some embodiments, a linker is further connected to one or more different types of active components. In some embodiments, the linker is covalently attached to the backbone of the polymer. In other embodiments, the linker is covalently attached to a side group of the polymer. In some embodiments, a component, such as a polypeptide, is directly linked to the backbone of the polymer, forming a polymer backbone conjugate.

When a peptide or another biologically active molecule is attached to the other end of the silane cross linker, it will have a dissociation constant ($K_d$), or binding affinity, that is specific to a given target molecule at a given set of conditions. In some embodiments, it may allow for reversible binding of one or more target(s). In some embodiments, the aforementioned target may be released back into a wound when used as part of the methods and devices contemplated herein. In some embodiments, ingredients may be added to the instillation solution to not only help dissociate the bound factor back into the wound environment but to also interact synergistically with the retained exudate element(s) for a modulating effect so that a favorable wound healing response is elicited. Types of instillation solutions are discussed in greater detail below.

Examples of instilled ingredients which may be used in some embodiments to dissociate bound molecules from the peptide linkers include: saline solutions, solutions with slightly acidic pH, slightly basic pH, solutions with various surfactants (i.e. polysorbate), EDTA or EGTA. In some embodiments, the fluid instilled to initiate the dissociation of the bound factors from the linker will depend upon the binding strength of the factor-linker complex, which is in turn determined by the dissociation constant. The dissociation constant may be modified by using knowledge of amino acid chemistry of the factor of interest to design a linker/peptide/aptamer.

One example of a modified dressing or wound insert is one capable of binding a metal, such as $Ca^{2+}$, wound derived or otherwise, and retaining it at the wound site. During the early phases of wound healing, $Ca^{2+}$ ions are typically released from the cells locally into the extracellular space. The resulting high $Ca^{2+}$ concentration is believed to be a positive effector of many cellular processes involved in wound healing such as adhesion, migration and differentiation. When a high $Ca^{2+}$ concentration is required or is beneficial to the wound bed, instillation or flushing with a solution containing a chelator (e.g., EDTA) may be used to disrupt the binding of $Ca^{2+}$ to the dressing and into the wound bed.

Another factor is transferrin, a blood plasma protein for iron binding. Chronic wound fluid has been shown to have significantly lower transferrin levels indicating that oxidative stress occurs in chronic wounds. It is known that free iron can play a role in the formation of free radicals. Without being bound by theory, high levels of free iron may contribute to exacerbation of tissue damage and delayed wound healing. Binding and concentrating transferrin onto the dressing can be used to sequester free iron in the wound bed with subsequent release with an appropriate instillation solution and subsequent removal with the exudate following the use of negative pressure. This specific time-dependent modulation of transferring and iron levels can provide a significant benefit to the patient. In an alternate view, the affinity of transferrin for iron is very high but is reversible in that it decreases progressively with decreasing pH below neutrality. If a need for localized iron concentration is necessary, instillation of a low pH solution can be used to unbind or release iron from transferrin.

Hyaluronan, or hyaluronic acid, is another possible target contemplated for use. Without being bound by theory, immobilizing and concentrating hyaluronan to the wound bed before instillation with an appropriate solution for release may be used to contribute to keratinocyte proliferation and migration and reduce collagen deposition, which in turn is known to lead to reduced scarring. Hyaluronan is also known for its free-radical scavenging function that could be beneficial as it is bound to the foam on the wound site.

Lactoferrin, known for its antimicrobial and anti-inflammatory properties, is another possible target for some of the embodiments. Secreted by endothelial cells, lactoferrin has been shown to have a synergistic effect with FGF2 in that there is a marked increase in their ability together to effect fibroblast migration and proliferation. Specifically designed polypeptide aptamers can be used to bind both LF and FGF2 and release them with an appropriate instillation solution in an opportune therapeutic timeframe.

TGFB-3 can be another target another possible target for some of the embodiments. This protein promotes reorganization of matrix molecules, resulting in an improved dermal architecture and reduced scarring. TGFB-3 is secreted in latent form that requires activation before it is functional. Activation of latent TGFB-3 occurs via binding to thrombospondin-1 (TSP-1). Therefore, TSP-1, may be used in some embodiments, as an ingredients in the instillation fluid to modulate TGFB-3 activity.

Possible other targets include calmodulin, S-100, thyroxine and cholate receptors, amongst many others.

In some embodiments, the therapeutic agent may be a crosslinked matrix. As an example, the matrix may be a crosslinked protein matrix, wherein the protein is an enzyme. The enzyme contains amine groups which can be used to connect enzyme molecules to each other. A crosslinker may be used to connect one enzyme molecule to another to form a matrix. Crosslinking of enzymes stabilizes, immobilizes, and protects the enzyme from degradation by proteases. The crosslinked matrix may be covalently attached to the foam.

Crosslinking agents that can be used to connect enzymes to form a crosslinked enzyme matrix include glutaraldehyde, the crosslinkers of Table I, and the crosslinker having formula (II).

Biologically active molecules, such as therapeutic agents, may be covalently attached to the foam through a crosslinker or through a crosslinker covalently attached to an adapter linked to the foam. Biologically active molecules may be attached by any physical or chemical methods. Examples of such methods may involve temperature, pressure, pH, radiation, light, UV light, freeze-drying, sterilization.

C. Uses of Modified Materials

The amine-functionalized polymeric materials discussed herein may have many applications in both medical and non-medical use. As a material in and of itself, the polymeric product is more hydrophilic than most other polyurethanes due to the copolymerization of hydrophilic aminoglycosides. This allows the polymeric materials to work well in communication with fluids. Thus, this material would provide a good platform for various textiles, diagnostics, protectants, and functionalization of various polymeric interfaces that operate with a fluid medium.

The polymeric material discussed herein provides the basis for a variety of functionalized materials and applications in the medical device industry. Since the amine-functionalized polymeric material has selective reactivity, these materials are relatively benign to living tissues and therefore biocompatible. The combination of fluid and biological compatibility provides a good base material for use in biomedical devices. As such, the copolymer discussed herein could provide the material basis for any medical device that comes into direct contact with the tissues of a patient, including but not limited to: a medical device coating; solid or semi-solid membranes; permeable, or semi-permeable membranes; interfacial layers, bead coatings, catheter or stent coatings, wound dressings, or any polymeric device that could benefit from being functionalized with the aforementioned therapeutic agents. As an example, a catheter may be coated with a functionalized polymeric material covalently attached with heparin.

Wound dressings provided herein comprising the amine-functionalized foam and one or more therapeutic agents may be used in various ways. As an example, there are at least six therapeutic modalities for employing the amine-functionalized wound dressings. They include sacrificial substrates, antimicrobials, sequestration, mimetics, and catch and release using peptides, and enzymes.

When the wound dressing comprises a sacrificial substrate attached to the foam, such as collagen, gelatin, or other protein or peptide, the wound dressing may be used to reduce matrix metalloprotein damage to healthy tissues. Antimicrobials, such as tetrammonium compounds or antimicrobial peptides, attached to the wound dressing may be used to target biofilms and inhibit microbial proliferation. With sequestration, critical inflammatory proteins may be sequestered or seized from the wound environment to prevent harmful biological processes. A mimetic is a molecule that imitates the structure of other important proteins in order to influence cellular processes. The catch and release mechanism can be carried out using peptides that are designed to trap specific protein targets. The process involves grabbing desirable proteins from the wound fluid and concentrating them along the surface of the foam to be released at a later time, for example with an instillation solution. Releasing the trapped proteins in a single bolus allows the user to trigger specific responses from the wound bed. Agents used for sequestration may comprise but are not limited to anti-sense oligomers, high affinity capture peptides, antibodies, and high affinity proteins. An example of sequestering agent is an anti-IL-1 antibody. Agents used for mimetics may comprise but are not limited to natural or synthetic derivatized biomolecules that resemble the epitopes of regulatory or structural molecules; these epitopes may comprise: structural, receptor-binding, dimerizing, co-factor binding, allosteric, or active site epitopes. An example of such an epitope mimetic is a synthetic cytokine or growth factor epitope, used to activate a cell receptor or signal protein. An example of a catch and release peptide comprises a natural or synthetic peptide that binds to a target protein.

The wound dressing may be covalently attached with enzymes that may perform physiological processes. The wound dressing may introduce or augment desirable enzymatic activity in the wound environment in a localized manner for a controlled period of time. The type of enyzme covalently attached to the wound dressing may vary. The enzymes on the wound dressings may be useful for debridement of tissues, biofilm mitigation, or wound healing. Some examples of debridement enzymes include bromelain, papain, collagenase, and trypsin. Biofilm mitigation may be based on enzymes that permanently modify bacteria-specific D-residues, such as D-amino acid oxidase, or enzymes such as carboxypeptidase A, which specifically cleaves bacterial peptides to disrupt communication between bacterial colonies. Other enzymes that aid wound healing, such as catalases, may be used to neutralize harmful oxygen radicals to limit ROS-mediated tissue injury. In other embodiments, the enzymatic agent could be, but is not limited to a protease, hydrolase, lyase, ligase, isomerase, transferase, oxidase, reductase, oxidoreductase, synthase, phosphatase, kinase, or polymerase. The wound dressing may be a multifunctional dressing comprising, for example, a debriding agent and an anti-biofilm agent.

In one embodiment, the wound dressing comprising an amine-functionalized polymer and an enzyme may be used as a debridement device to remove devitalized tissue from the wound bed. In another embodiment, the wound dressing comprising an amine-functionalized polymer and an enzyme may be used with or without negative pressure wound therapy and with or without an instillation solution.

In other embodiments, the therapeutic agent attached to the amine-functionalized polymer may be a crosslinked enzyme matrix. Crosslinking stabilizes and protects the enzyme from degradation by other proteases. A wound dressing comprising a crosslinked enzyme matrix may be used with negative pressure wound therapy and/or an instillation solution or other harsh conditions without the enzyme matrix coming off in the wound environment.

The wound dressings described herein may comprise any therapeutic agent. In some embodiments the wound dressings may be used with and without negative pressure wound therapy and with or without an instillation solution.

The amine modified polymers described above and materials made therefrom may be used for a variety of purposes, including to (a) capture and concentrate biological targets in the wound environment, (b) specify the chemical nature of the binding, and/or (c) dictate the orientation with which the target factors are presented to the cells. As discussed in greater detail in the Examples section below, modified polyurethanes, including peptide modified GranuFoam™ (GF), a type of ROCF, may be used to capture specific protein targets in vitro.

In some embodiments the modified polymers may be used to bind protein targets in the wound environment without inhibiting their signaling capabilities or other functions. Such modified polymers may be used as part of a dressing or wound insert, for example, to capture and increase concentrations of biologically active proteins across a wound bed of a patient, for example, to strengthen or activate a targeted biological response.

In some embodiments, such a dressing may be used to concentrate proteins of interest such as vascular endothelial growth factor in the wound bed to trigger angiogenesis and tubule formation. Additionally, antibodies or peptides may be designed to antagonize or sequester proteins that adversely affect the healing process, such as matrix metalloproteinases and inflammatory mediators. Dressings made of such modified polymers may thus be used, in some embodiments, to modulate various biological pathways or to manage the presence of unwanted bioactive molecules or enzymes in the wound environment.

In addition to dressings, modified polymers, including those using a heterobifunctional silyl-modified linker and a polyurethane-based polymer or copolymer, may also be used in a wide array of other materials, matrixes and biomedical devices, including catheters. In such embodiments, they may be used to conjugate a variety of biologically active components, including antimicrobial compounds. The application of these materials to a negative pressure-based therapy is discussed in greater detail below.

Materials may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

It should be recognized that the formation of variable anion and cation species is an expected outcome of the chemical processes described herein, so long as the dominant species generated is pharmacologically acceptable.

Additional examples of pharmaceutically acceptable salts and their methods of preparation and use are presented in *Handbook of Pharmaceutical Salts: Properties, and Use* (2002), which is incorporated herein by reference.

D. Preparation of Inserts Comprising Foam Materials Based

In another aspect, foam-based polymers may be physically and/or chemically treated, coated or manipulated before or after they are covalently linked to an active component. Some embodiments of making modified wound inserts comprise: compressing (and/or felting) at least a portion of a foam. Some embodiments comprise: treating (e.g., by applying heat, or activating a coating that has been applied to) the compressed foam such that the foam remains substantially compressed in the absence of an external compressive force. For example, in some embodiments, treating comprises heating the foam (e.g., foam) to an elevated temperature sufficient to reduce resiliency of the foam. For example, the foam can be heated to a temperature at which resiliency of the foam is reduced and/or relaxed, but that is below the melting temperature of the foam (e.g., such that the foam is not degraded by the elevated temperature). In this way, the foam can be compression set using heat and pressure (compressive force) to relax compressive strains developed in the foam. Generally, high temperatures are used to achieve the compression set. To achieve the desired "set" such that resiliency of the foam is reduced and/or the foam remains substantially compressed in the absence of a compressive force, temperatures can range from 158 degrees Fahrenheit to 482 degrees Fahrenheit (e.g., equal to, less than, greater than, or between any of: 140, 160, 180, 200, 220, 240, 260, 280, 300, 320, 340, 360, 380, 400, 420, 440, 460, 480, 500 degrees Fahrenheit, depending upon the particular foam used). The foam may also be put through a cooling cycle to help retain the set introduced. For example, the foam may be cooled to a temperature below room or ambient temperature (e.g., to or in a temperature equal to, less than, greater than, or between any of: 0, 5, 10, 15, 20, 25, 30, 35, 40, 45, 50, 55, 60, 65, or 70 degrees Fahrenheit). In some embodiments of the present methods of forming a modified wound insert, the foam is disposed between two heated plates or platens (e.g., in a plate or platen press and/or where the plates are heated to a temperature sufficient to reduce the resiliency of the foam); and the press is actuated to move the plates toward one another (e.g., perpendicular to thickness 320 of thick portions 304) such that the foam is compressed to the desired overall thickness or degree of compression). Such a press can be electrically, mechanically, and/or hydraulically operated.

Some embodiments of the present methods of making modified wound inserts also comprise: cooling the foam (e.g., after heating the foam) such that the compressed portion of the foam remains substantially compressed at room temperature (e.g., at a temperature of 72 degrees Fahrenheit) in the absence of a compressive force. In other embodiments, cooling the foam includes cooling a coating that has been applied to the foam such that the compressed portion remains substantially compressed in the absence of a compressive force at a temperature or temperature range equal to, less than, greater than, or between any of: 10, 20, 30, 40, 50, 60, 70, 80, 90, 100, 110, 120, 130, 140, and/or 150 degrees Fahrenheit.

Thick and thin regions in the foam can be formed by any suitable methods, such as, for example, laser cutting or the like. Such methods are taught, for example, by U.S. Patent Application Publication 2011/0178451, which is incorporated herein by reference.

In such embodiments, the coating can be dispersed through the foam, such as, for example, by spraying the foam with the coating, dipping the foam in the coating, and/or any other suitable way of dispersing the coating in the foam. In some embodiments, for example, the foam can be coated with a material that has a transition temperature (e.g., melting point, glass transition, etc.) that occurs at a relatively low temperature (e.g., lower than the foam alone), or that develops stiffness as it dries. In some embodiments, the coating can be configured to enable the foam to be compressed (and/or compression set) at lower temperatures (e.g., without heating), such that the coating becomes stiff or otherwise resistant to expansion as it cools or dries to hold the foam in its compressed configuration. For example, a fluid adhesive may be applied to thick portions before compressing the foam and permitted to dry before removing the compressive force, such that the dried adhesive will resist expansion from the compressed thickness. In other embodiments, the coating can be configured to compression set the foam such that the compression is reversible (e.g., at least partially and/or completely reversible) such that the foam can expand (e.g., after placing in or on a wound) as it warms or absorbs water. In some embodiments, the coating comprises a cross-linkable polymer and/or activating comprises exposing the coating to light and/or elevated temperature (e.g., above ambient temperature, such as, for example, a temperature sufficient to cause at least part of the cross-linkable polymer to cross-link) to cause at least some portion of the cross-linkable polymer to become modified.

Examples of suitable coatings include cross-linkable polymers that contain n-methylol acrylamide (NMA). NMA is a monomer that may be co-polymerized with many other monomers (such as acrylics & vinyls). On heating, (e.g., to about 140° C.), NMA reacts with itself and other hydroxyl-containing groups (e.g., carboxyl). Similarly, urea formaldehyde, melamine formaldehyde, and/or phenol formaldehyde can be caused to react with themselves and other hydroxyl-containing polymers to form crosslinks. Other crosslinking agents may include, for example, modified ethylene ureas, which react with hydroxyl-containing polymers at elevated temperatures to crosslink them. Other crosslinking agents can include peroxides which will cross-link most polymers at elevated temperatures. Polymers containing hydroxyl and carboxyl groups may also be combined, and, when heated, may form polyester crosslinks. Additionally, epoxy prepolymers can be used that have low reactivity at room temperatures, and when heated, react quickly to form an epoxy polymer with crosslinks. Similarly, polymeric isocyanates may be used that will only react significantly fast at elevated temperatures and in presence of hydroxyl groups, amines, or moisture to form polyurethanes or polyureas.

In some embodiments, a combination of high-density regions and low-density regions cooperate to provide various characteristics for the present modified wound inserts.

For example, the high-density regions have a smaller aggregate cell size and increased cell density, such that the high-density regions have improved wicking function and more-effectively transmit fluid (e.g., draw fluids away from the wound surface and/or communicate fluid from a fluid source to the wound surface more effectively than the low-density regions. The high-density regions are generally also mechanically stronger than the low-density regions, such that the high-density regions can provide structural support for the low-density regions and/or the modified wound insert as a whole (e.g., such that the modified wound insert is resistant to tearing in directions that are not parallel to the low-density regions). Additionally, the low-density regions have a larger effective cell or pore size such that the low-density regions are less-susceptible to clogging. Especially when a negative pressure is applied to draw fluid and/or exudate away from the wound and through the modified wound insert, the larger pore size of the low-density regions may permit fluids to be drawn through the low-density regions at a higher velocity than the fluid is drawn through the high-density regions, such that particulate and granular matter are drawn to and/or through the low-density to discourage and/or decrease the likelihood of clogging in the high-density regions. In some embodiments, the foam can also be coated with a hydrophilic material to improve wicking properties of the modified wound insert.

The low-density regions may also be configured to permit the wound dressing to bend and/or otherwise conform to a wound. For example, the low-density regions can be relatively easier to bend (and/or less resilient when the modified wound insert is bent or folded along a low-density region) such as to double over a modified wound insert, and/or to conform a modified wound insert to additional hardware such as plates, pins, or the like.

Typical single-density foam modified wound inserts are isotropic such that under negative pressure, a typical single-density foam modified wound insert will contract proportionally in all directions. In some embodiments, the present modified wound inserts may also be configured to be anisotropic, such that the present modified wound inserts can be configured to mechanically assist with wound closure. For example, low-density regions are less-dense (and will compress more under negative pressure) than high-density regions. As such, if negative pressure is applied to modified wound insert, low density regions will contract more than high-density regions, such that high-density regions will be drawn together and modified wound insert will contract laterally more than longitudinally. In other embodiments, the present modified wound inserts can be configured to have alternating and sequentially larger closed ring-shaped high-density regions and low-density regions, such that under negative pressure, the modified wound insert will contract laterally inward to its own center.

In some embodiments, thick portions, thin portions, high-density regions, and/or low-density regions can be coated and/or printed (either before or after compression) to enhance the hydrophilic or hydrophobic properties of individual regions of the foam or of the foam as a whole. Such coated regions may also contain and/or be coated with other additives, such as antibiotics, or blockage-reducing agents.

In some embodiments, wound dressings comprise a wound dressing configured to be positioned on a wound (e.g., 26 of FIG. 1) of a patient (e.g., 30) and/or on or in contact with the wound surface (e.g., 42).

The wound dressings described herein comprising an amine-functionalize foam may further comprise a backing or drape, covering the polymer foam substrate. The drape may be occlusive and may extend beyond the foam. The drape may include an adhesive portion. The adhesive portion of the backing may extend over the foam for adhering the wound dressing directly to the area around the wound site. The wound dressing may include an absorbent layer between the foam and the backing.

Some embodiments of the present wound-treatment methods comprise: positioning a modified wound insert (e.g., any of the present modified wound inserts such as 34) on a wound (e.g., 26) of a patient (e.g., 30), where the modified wound insert comprises a foam (e.g., 116). In some embodiments, the foam is sterile (e.g., substantially free of microbes and/or bacteria). Some embodiments further comprise: coupling a drape (e.g., 38) to skin (e.g., 46) adjacent the wound such that the drape covers the modified wound insert and the wound, and forms a space between the drape and the wound. Some embodiments comprise: applying negative pressure to the wound through the wound dressing (e.g., through the modified wound insert). In some embodiments, applying negative pressure to the wound comprises activating a vacuum source (e.g., apparatus 14 of FIG. 1, or vacuum source 200 of FIG. 3) that is coupled to the wound dressing. Some embodiments comprise: delivering a fluid to the wound through the wound dressing. In some embodiments, delivering a fluid comprises activating a fluid source (e.g., fluid source 248 of FIG. 3) that is coupled to the wound dressing.

Some embodiments of the present wound-treatment systems comprise either embodiment of system 10 (or any subset of components of either embodiment of system 10), and one or more of the present modified wound inserts and/or wound dressings.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

It will be understood that the benefits and advantages described above may relate to one embodiment or may relate to several embodiments. It will further be understood that reference to 'an' item refers to one or more of those items, unless otherwise specified.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of the present disclosure.

E. Devices Comprising an Modified Wound Insert

The modified polymers described above and materials made therefrom may be used for a variety of purposes, including to (a) capture and concentrate biological targets in the wound environment, with the option to release back into the wound bed, (b) specify the chemical nature of the binding, and/or (c) dictate the orientation with which the target factors are presented to the cells.

A dressing or wound insert made for an modified polymer may be used together with negative pressure wound therapy. In some embodiments, compatible foam coated with aptamers or small peptide linkers (ligands) which select for beneficial molecules in the wound fluid as it passes through the foam would thereby prevent their removal into the negative pressure wound therapy canister. Appropriate molecules for selection from wound fluid include metabolites, growth factors, chemokines and cytokines which would not impede fluid flow through the negative pressure wound therapy dressing. In some embodiments, appropriate linkers would bind the wound fluid molecules in such an orientation that the "active site" of the wound fluid molecule is still available for eliciting a biological response. For example, one such molecule may be VEGF. VEGF has specific sites on the molecule that bind to cellular receptors. The binding of the VEGF molecule to the cellular receptor may be used to initiate a biological response, typically angiogenesis.

In some embodiments, the methods taught herein may be used to bind to molecules chemotactic to macrophages such as MCP1, which may be used to stimulate macrophage migration into the wound and thereby progress the wound from a chronic to a healing state. In some embodiments, PDGF or collagen fragments could be bound during the proliferative or late inflammatory phases to stimulate the migration of fibroblasts into the wound. Stimulating the migration of macrophages and then fibroblasts into the wound may assist in the progression of the wound through the inflammatory phase and into the proliferative phase of wound healing. In some embodiments, Nitric Oxide Synthase could be bound from the wound fluid to stimulate perfusion. This may help to promote healing by allowing a higher level of nutrients into the wound. In some embodiments, anti-inflammatory cytokines such as IL4 or IL10 could be bound to decrease inflammation, thus progressing the wound more quickly through the inflammatory and into the proliferative phase of healing. DNA fragments could also be bound to the dressing. In some embodiments, the binding of highly charged DNA could enable current to be passed through the dressing. Electrical stimulation has been used for many years in the treatment of wounds. Therefore, binding DNA to the wound dressing may allow for the application of current to the wound.

Figure 1:
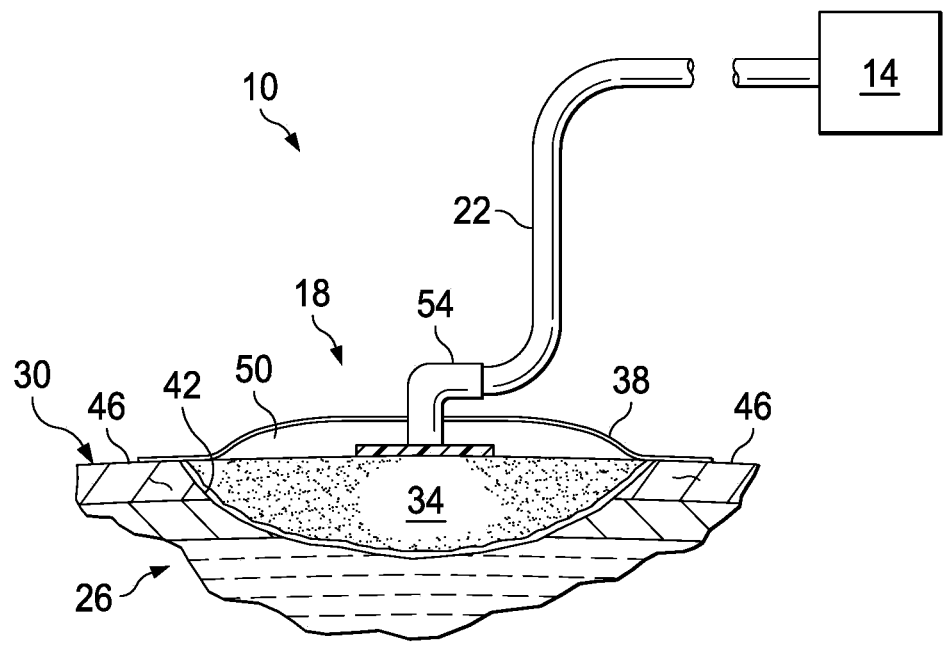
FIG. 1 depicts a side view of one embodiment of a wound dressings of the embodiments having one of the present modified wound inserts and coupled to a wound site and to a wound treatment apparatus.

Referring now to the drawings, and more particularly to FIG. 1, shown therein is an embodiment of one of the present wound treatment system 10. In the embodiment shown, apparatus 10 comprises a wound-treatment apparatus 14, and a wound dressing 18 coupled to apparatus 14 by a conduit 22. As shown, dressing 18 is configured to be coupled to (and is shown coupled to) a wound 26 of a patient 30. More particularly, in the embodiment shown, dressing 18 comprises a modified wound insert 34 and a drape 38. As shown, modified wound insert 34 is configured to be positioned (and is shown positioned) on wound 26 (e.g., on or adjacent to wound surface 42), and/or drape 38 is configured to be coupled to (and is shown coupled to) skin 46 of the patient adjacent to wound 26 such that drape 38 covers modified wound insert 34 and wound 26, and forms a space 50 between drape 38 and wound 26 (e.g., wound surface 42).

Apparatus 14 can comprise, for example, a vacuum source configured to be actuatable (and/or actuated) to apply negative pressure (e.g., via conduit 22) to wound dressing 18, a fluid source configured to be actuatable (and/or actuated) to deliver (e.g., via conduit 22) a fluid (e.g., an installation fluid such as a medicinal fluid, antibacterial fluid, irrigation fluid, and or the like) to wound dressing 18. System 10 can be implemented and/or actuated and/or coupled to patient 30 in any of various configurations and/or methods similar to those described in the prior art. For example, various wound therapy systems and components are commercially available through and/or from KCI USA, Inc. of San Antonio, Tex., U.S.A., and/or its subsidiary and related companies (collectively, "KCI").

Conduit 22 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduit 22 can comprise, for example, a first lumen for the application of negative pressure and/or fluid delivery, and at least one additional lumen for coupling to pressure sensor(s) to sense pressure or negative pressure between drape 38 and surface 42. In some embodiments, conduit 22 can comprise multiple lumens (e.g., as in a single conduit with a central lumen for application of negative pressure and/or fluid delivery, and one or more peripheral lumens disposed adjacent or around the central lumen such that the peripheral lumens can be coupled to a pressure sensor to sense a pressure or negative pressure between drape 38 and surface 42 (e.g. in space 50). The lumens may be arranged with a central lumen and other lumens disposed radially around the central lumen, or in other suitable arrangements. The lumens may also be provided in separate conduits. In the embodiment shown, system 10 further comprises a wound dressing connection pad 54 configured to be coupled (and is shown coupled) to conduit 22. One example of a suitable connection pad 54 is the "V.A.C. T.R.A.C.® Pad," commercially available from KCI. One example of a suitable drape 38 includes the "V.A.C.® Drape" commercially available from KCI.

Figure 2:
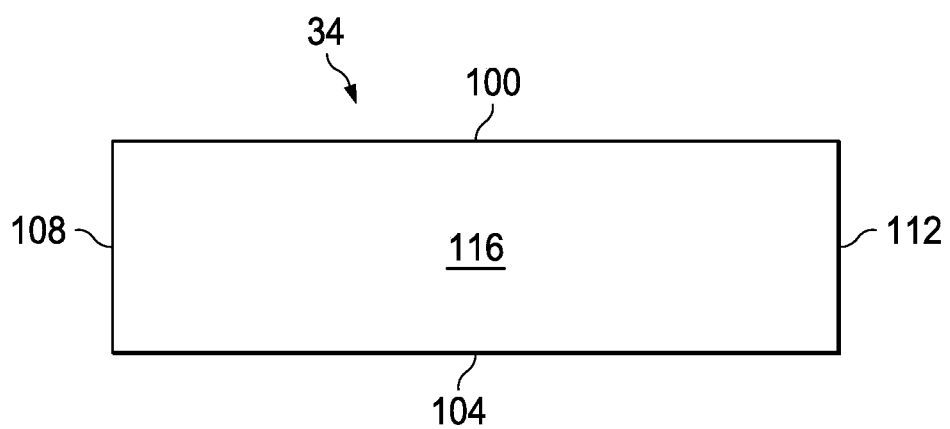
FIG. 2 depicts an enlarged side view of the modified wound insert of FIG. 2.

Referring now to FIG. 2, a side view of a modified wound insert 34 is shown. Modified wound insert 34 has an upper side 100, a lower side 104, lateral sides 108, 112 and interior volume 116. Although only one side is shown of modified wound insert 34, it will be understood by those of ordinary skill in the art that modified wound insert 34 includes a three-dimensional rectangular volume having a depth extending perpendicular to the side shown. In other embodiments, modified wound insert 34 can have any suitable shape, such as, for example, a round cylindrical shape, a fanciful shape, or may be trimmed to fit an irregular shape of a wound (e.g., 26 and/or wound surface 42). Modified wound insert 34 can comprise a foam, such as, for example, open-celled foam (which may also be reticulated).

Embodiments of the present wound treatment methods may be better understood with reference to FIG. 1, which depicts a schematic block diagram of one embodiment of system 10. In the embodiment shown, wound dressing 18 is coupled to apparatus 14, and apparatus 14 comprises a vacuum source 200 (e.g., a vacuum pump and/or the like) coupled to a canister 204 (e.g., configured to receive exudate and or the like from wound dressing 18) by way of a conduit 208. In the embodiment shown, apparatus 14 further comprises: a pressure sensor 212 having a first pressure transducer 216 coupled to conduit 208 by way of conduit 220 and/or tee-fitting 224, and a second pressure transducer 228 coupled to canister 204 and/or wound dressing 18 by way of conduit 232. Pressure sensor 212 is configured to sense the negative pressure in wound dressing 18, and/or any of the various lumens (e.g., within conduits) coupled to wound dressing 18, pressure sensor 212, and/or vacuum source 200.

In the embodiment shown, apparatus 14 further comprises a pressure release valve 236 coupled to conduit 232. Further, in the embodiment shown, canister 204 and vacuum source 200 are coupled to wound dressing 18 by way of conduit 240; and/or canister 204 can comprise a filter 244 at or near an outlet of canister 204 to prevent liquid or solid particles from entering conduit 208. Filter 244 can comprise, for example, a bacterial filter that is hydrophobic and/or lipophilic such that aqueous and/or oily liquids will bead on the surface of the filter. Apparatus 14 is typically configured such that, during operation, vacuum source 200 will provide sufficient airflow through a filter 244 that the pressure drop across filter 244 is not substantial (e.g., such that the pressure drop will not substantially interfere with the application of negative pressure from wound dressing 18 from vacuum source 200).

In the embodiment shown, apparatus 14 further comprises a fluid source 248 coupled to wound dressing 18 by way of a conduit 252 that is coupled to conduit 240 such as, for example, by way of a tee- or other suitable fitting 256. In some embodiments, tee fitting 256 can comprise a switch valve and/or the like such that communication can be selectively permitted between wound dressing 18 and vacuum source 200, or between wound dressing 18 and fluid source 248. In some embodiments apparatus 14 comprises only one of vacuum source 200 and fluid source 248. In embodiments of apparatus 14 that comprise only fluid source 248, canister 204 and/or pressure sensor 212 can also be omitted. In various embodiments, such as the one shown, conduit 232 and/or conduit 240 and/or conduit 252 can be combined and/or comprised in a single multi-lumen conduit, such as is described above with reference to FIG. 1. In some embodiments, fluid source 248 is coupled directly to wound dressing 18 (e.g., conduit 252 is coupled one end to wound dressing 18, such as via connection pad 54, and conduit 252 is coupled on the other end to fluid source 248; and conduit 252 is not coupled to tee fitting 256).

Figure 3:
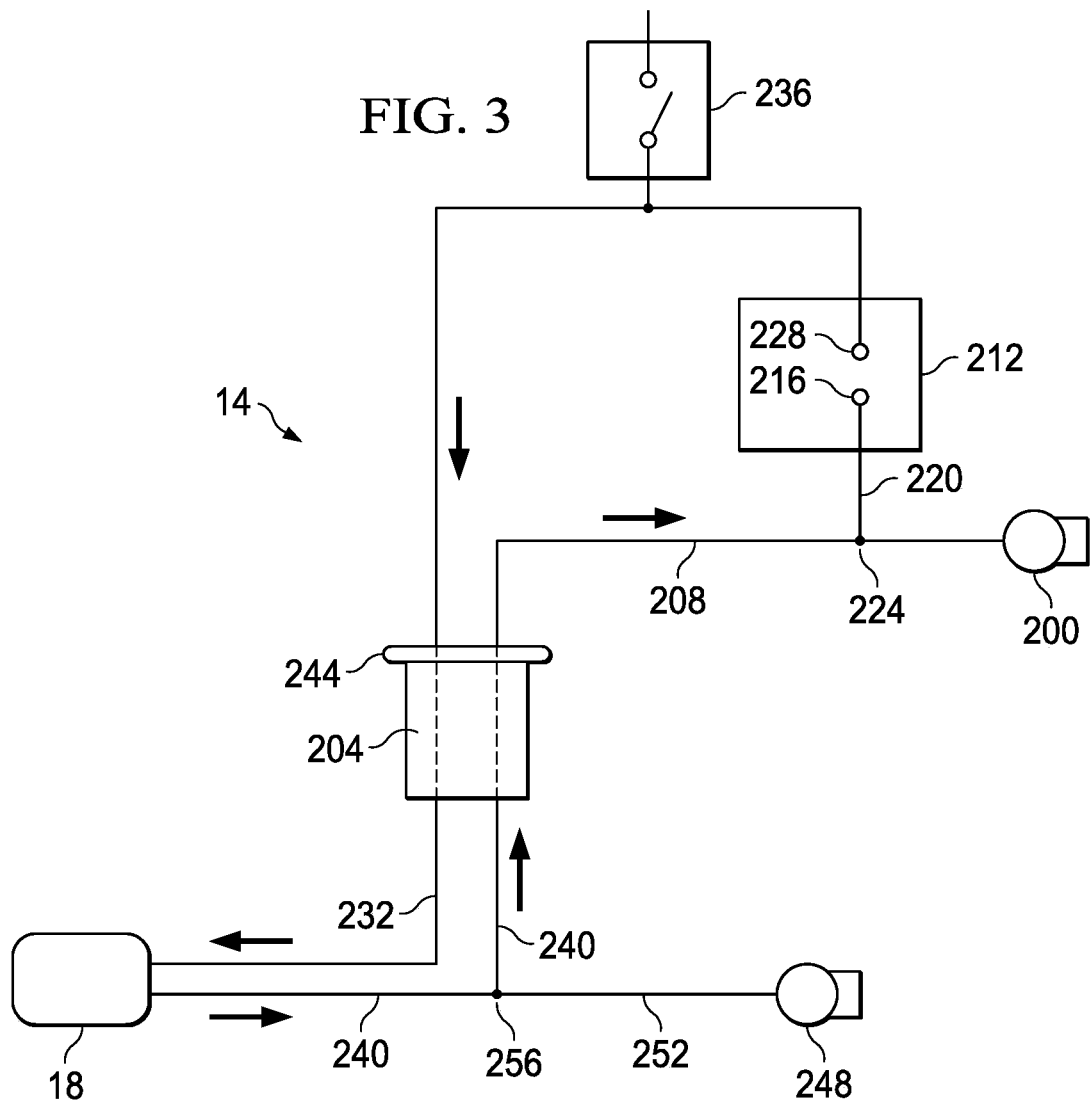
FIG. 3 depicts a schematic block diagram of one embodiment of a wound treatment apparatus that can comprise and/or be coupled to and/or be used with the present wound dressings and/or modified wound inserts.

In various embodiments, such as the one shown in FIG. 3, apparatus 14 can be configured such that as soon as liquid in the canister reaches a level where filter 244 is occluded, a much-increased negative (or subatmospheric) pressure occurs in conduit 208 and is sensed by transducer 216. Transducer 216 can be connected to circuitry that interprets such a pressure change as a filled canister and signals this by means of a message on an LCD and/or buzzer that canister 204 requires emptying and/or replacement, and/or that automatically shuts off or disables vacuum source 200.

Apparatus 14 can also be configured to apply negative (or subatmospheric) pressure (e.g., continuously, intermittently, and/or periodically) to the wound site, and/or such that pressure relief valve 236 enables pressure at the wound site to be brought to atmospheric pressure rapidly. Thus, if apparatus 14 is programmed, for example, to relieve pressure at ten-minute intervals, at these intervals pressure relief valve 236 can open for a specified period, allow the pressure to equalize at the wound site, and then close to restore the negative pressure. It will be appreciated that when constant negative pressure is being applied to the wound site, valve 236 remains closed to prevent leakage to or from the atmosphere. In this state, it is possible to maintain negative pressure at the wound site without running and/or operating pump 200 continuously, but only from time to time or periodically, to maintain a desired level of negative pressure (i.e. a desired pressure below atmospheric pressure), which is sensed by transducer 216. This saves power and enables the appliance to operate for long periods on its battery power supply.

In some embodiments, factors may be removed, or their concentration modulated, using electrical pulses, light, ultrasound and temperature.

F. Instillation Solutions

In some embodiments dressing made from the amine modified polymers disclosed herein may be used together with wound instillation solutions, for example in the application of a negative pressure treatment to a patient's wound. In some embodiments, the instillation solution comprises ingredients to help release or modulate the release of the factors bound to the foam to the wound site.

Examples of instilled ingredients which may be used in some embodiments to dissociate bound molecules include: saline solutions, pharmaceutically acceptable salt solutions, Dakin's solutions, PHMB solutions, acetic acid, zwitterionic detergent solutions, solutions with slightly acidic pH, solutions with slightly basic pH, solutions with various surfactants (i.e. tween, SDS, polysorbate), solutions with slight ionic charge, EDTA, or EGTA. In some embodiments, the fluid instilled to initiate the dissociation of the bound factors from the linker will depend upon the binding strength of the factor-linker complex, which is in turn determined by the dissociation constant. The dissociation constant may be modified by using knowledge of amino acid chemistry of the factor of interest to design the linker/peptide.

In some embodiments, the instillation solution comprises hypochlorous acid (HOCl) and hypochlorite ion. Both are examples of effective antimicrobial agents for biocidal action. For example, HOCl is typically capable of killing a broad spectrum of microbes (e.g., fungus, bacteria, viruses, fungus, yeast, and the like); often in a relatively short period of time (e.g., is capable of killing greater than 99% of microbes within a period of less than 10 seconds). Such antimicrobial agents can be generated or formed by a combination of the present reactive agents and fluid (e.g., water and/or aqueous solution, such as, for example, saline solution) and may be more effective and/or more versatile than antibiotics and other commonly used antimicrobial agents used in wound treatment in the past. For example, antibiotics may be bacteria-specific such that testing may be required to determine a suitable antibiotic to use for a specific wound or infection; and/or such that antibiotics may have only limited effectiveness for individual wounds and/or infections (e.g., where testing is not performed and/or where a wound is infected with a plurality of different bacteria). Such testing may take as long as several days to determine an appropriate antibiotic, delaying treatment or selection of an effective antibiotic. Additionally, bacteria may develop resistance to antibiotics, such that antibiotics may have reduced effectiveness after an amount of time. Further, antibiotics are typically administered intravenously (systemically) such that antibiotics may kill beneficial bacteria (e.g., in a patient's digestive system) and/or may cause organ damage (e.g., to a patient's liver).

In contrast, the reactive agents (and/or antimicrobial products of the reactive agents) of the present embodiments can be configured to have a broad-spectrum killing power that will kill a variety of microbes (e.g., fungus, bacteria, viruses, fungus, yeast, etc.). Additionally, the present reactive agents (and/or antimicrobial products of the reactive agents) can be delivered locally (preventing systemic damage or other side effects to organs and the like).

However, due to the reactivity of HOCl or OCl⁻ with oxidizable organic substances, its utility in wound care applications has previously been limited. For example, prior art methods of generating hypochlorous acid have required electrolysis of saltwater or the like (e.g., with expensive equipment at a patient's bedside). By way of another example, commercially available chemicals (e.g., bleach) have a hypochlorous acid concentration of 5% or greater, which is too high to permit medical uses (e.g., will cause cytoxicity). Additionally, at suitable medical concentrations (e.g., 2-20 mM hypochlorous acid solutions), approximately 99% or more of the solution is water, such that shipping is more expensive and/or more difficult than necessary. Further, storage of hypochlorous acid solutions is difficult, as reactions with containers typically degrade or reduce the concentration of the hypochlorous acid solution. However, the present wound inserts can be deposited with reactive agents (have reactive agents deposited in the foam of the wound inserts) such that upon application of a fluid such as saline or water, OCl (and/or ClO⁻) is released (e.g., to form hypochlorous acid) and delivered to a wound for biocidal action.

EXAMPLES

The following examples are included to demonstrate preferred embodiments. It should be appreciated by those of skill in the art that the techniques disclosed in the examples which follow represent techniques discovered by the inventor to function well in the practice of the products, compositions, and methods described herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Preparation of Amine-Functionalized Polyurethane Foam

In the construction of this new foam material, neomycin (FIG. 4), an aminoglycoside, was co-polymerized with a polyol into a toluene diisocyanate backbone, producing a white, reticulated open celled foam (FIG. 5) that withstood 40 Kgy gamma sterilization. The neomycin modified foam also had good tensile strength and absorbed and retained water.

The 0.001-40 phr Neomycin foam prototypes showed reactivity with their primary amine groups. The reactivity of the amine groups was verified by incubating the foams with a dye that binds to primary amine groups. The more amine, the more fluorescence observed due to the dye. After binding the dye, the foams were measured for fluorescence and photographed in the fluorescent microscope (FIG. 6). The relative fluorescence units observed by fluorometer and the photos collected by fluorescent microscopy provided evidence of the amine functionality of the foam. When measured by fluorescence, the 10 phr neomycin foam had the highest amine content, 74868 RFUs. It is important to point out that this was twice the amount of RFU's observed with the 30 phr chitosan foam made by a professional foam manufacturer. 5 phr neomycin yielded 43632 RFUs, which was also substantially better than 36562 RFUs produced by the chitosan foam. The Base Polyurethane in this study consisted of polyol and TDI (no amines), so it was used as a negative control and yielded 7591 RFUs. At 15 phr, neomycin began to aggregate forming a paste that did not disperse well, thus the polymerization was poor. Thus, an ideal neomycin range may be between about 0-40 phr.

Neomycin polymerizes well with isocyanate chemistry due to the —OH groups and amine groups that allow it to copolymerize with the toluene diisocyanate. When the reaction occurs, the —OH and —NH2 groups polymerize with isocyanate, but a significant portion of the primary the primary amine groups (NH$_2$) remain accessible for further chemical reactions. Leaving the amines accessible is important because it will enable the crosslinker chemistries depicted in Table 1 above are possible adaptor molecules that can used for linkage of various biologically active compounds (e.g., proteins) to the modified foams. To summarize Table 1, amine functionalization of foams will allow for a wide array of novel crosslinker chemistries that can be used to further modify the foam.

Example 2: Amine-Functionalized Polyurethane Foam Containing Bromelain (Enzyme Protease Dressing (EPD))

The co-polymer was made by combining water, toluene diisocyanate, aminoglycoside, polyol, surfactant, and catalysts. Once polymerization was complete, the foam was cured and washed with deionized water. Next the therapeutic protein matrix was crosslinked and conjugated to the foam, creating the EPD. The EPD was subsequently washed and subjected to several physical and biochemical tests.

Analysis

The testing regimen for the EPD consisted of scanning electron microscopy (SEM, FIG. 7), biochemical tests (FIG. 8), and physical model tests. First, 250× photos of the enzyme-coated foams were collected to confirm the absence or presence of the coating. Second, biochemical tests were performed to measure the functionality of the enzymes after crosslinking. Next, EPD prototypes were applied to tissue models to observe proteolytic activity.

SEM Analysis of the EPD

Figure 7A:
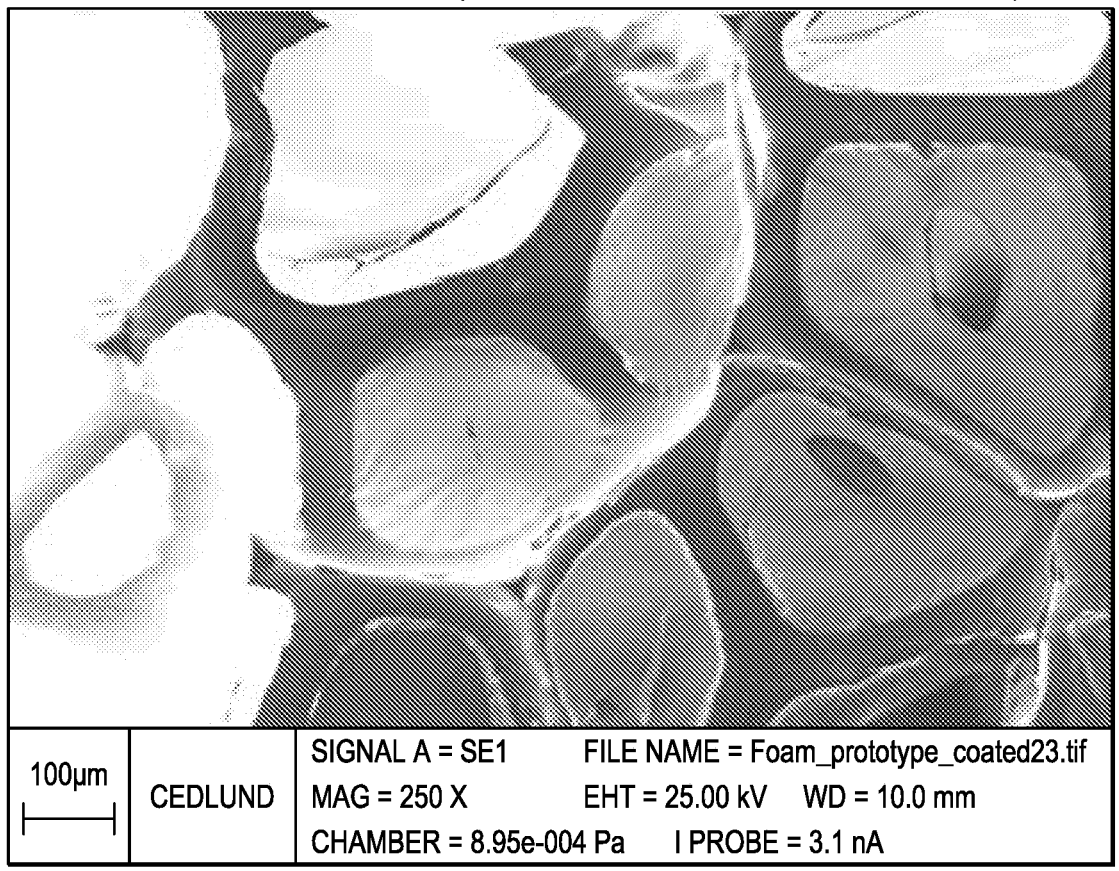
FIGS. 7A AND 7B depict SEM analysis of the Enzyme Protease Dressing (EPD) at 250×.
Figure 7B:
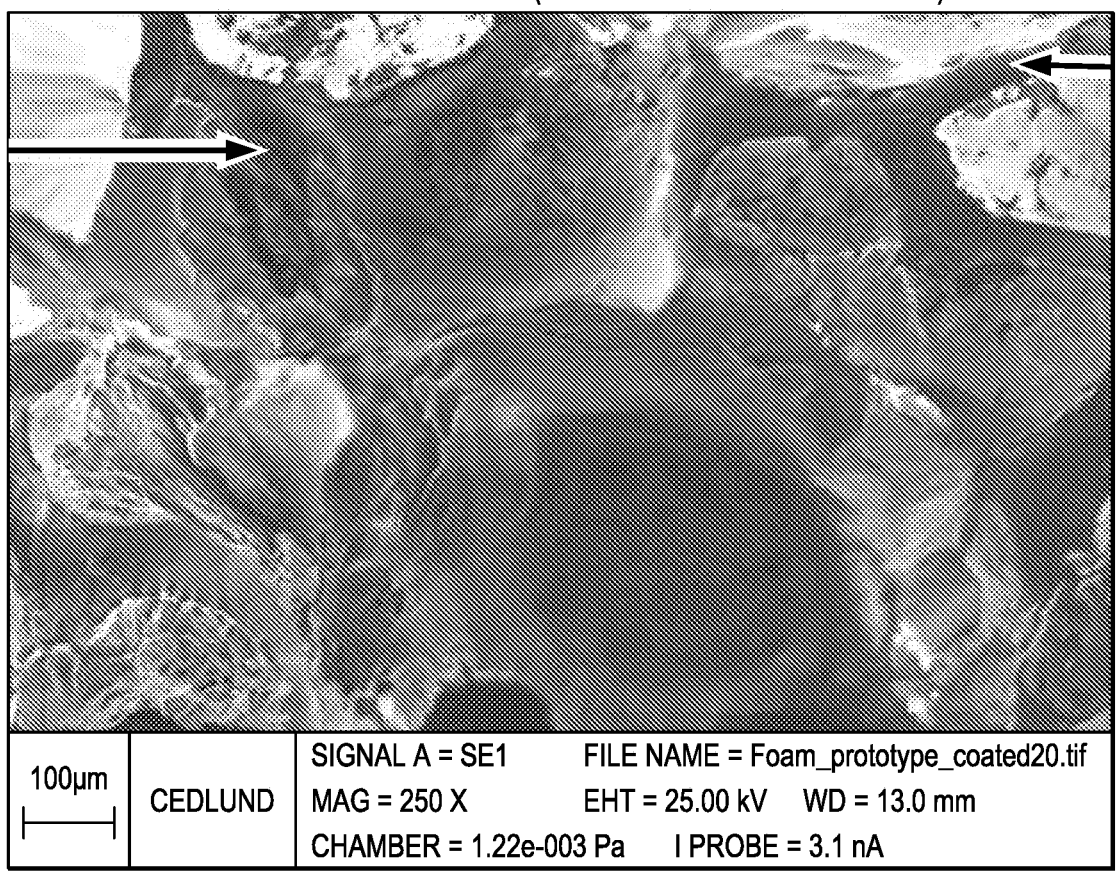

Images of the coated and uncoated foams with the SEM at 250× were obtained. FIG. 7A shows uncoated amine functionalized polyurethane foam substrate with smooth struts and surfaces. FIG. 7B shows the amine-functionalized polyurethane foam substrate with a covalently bound enzyme matrix (arrows). The enzyme matrix appears as coarse plaques that coat the foam surface. FIG. 7B confirms that the amine-functionalized foam is covalently coated with the enzyme.

Biochemical Tests

Figure 8:
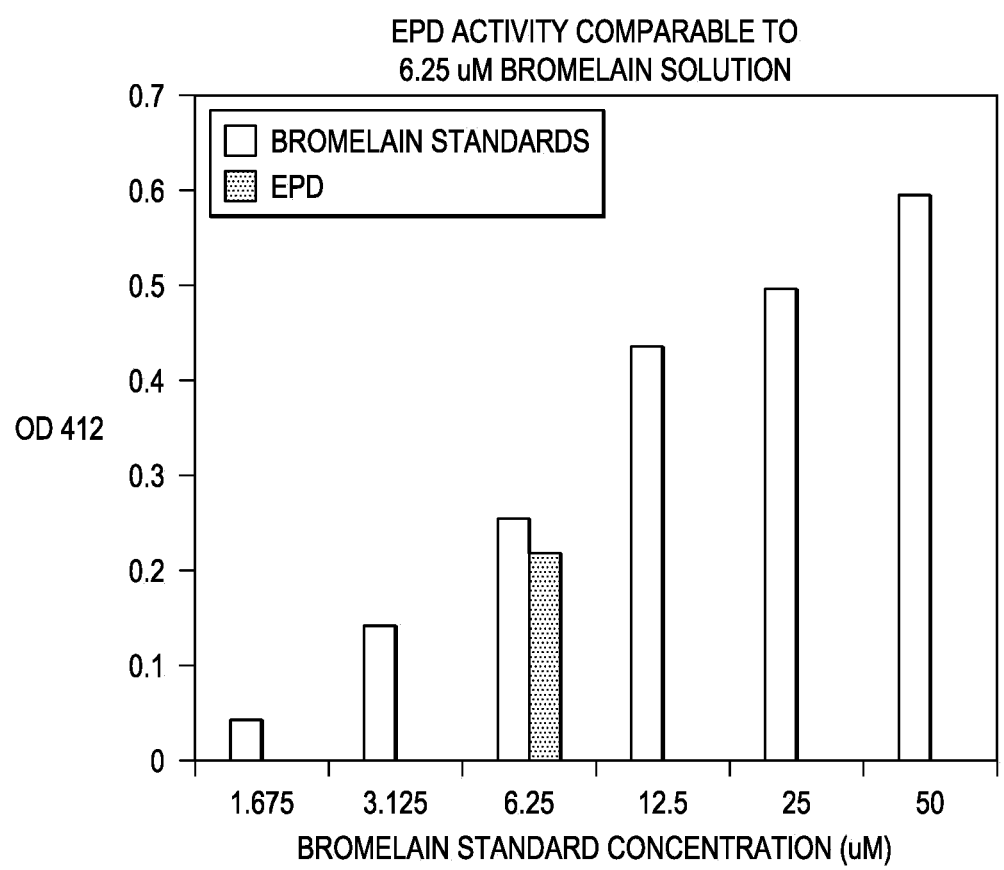
FIG. 8 depicts biochemical tests comparing EPD activity and 6.25 µM bromelain standard.

Bromelain is a cysteine protease enzyme that cuts proteins and peptides at specific amino acid sequences. EPD performance was measured in a biochemical assay against a published cysteine protease substrate. In this format, the bromelain cuts the substrate, making the substrate change into a yellow color. As more substrate is cut, more yellow color develops. The extent of the color formation (spectrophotometry at OD 412) can be measured to describe the amount of cutting performed by the enzyme. FIG. 8 compares EPD activity with bromelain standard. EPD performed roughly equivalent to the 6.25 uM bromelain standard. The standards were prepared by dissolving crude Bromelain powder in reaction buffer and testing the solutions against the substrate. Consequently, these data indicate that the covalently bound bromelain enzyme was functional after crosslinking to the foam.

Physical Model Tests

The physical model is a useful tool for visualizing the proteolytic activity of the EPD. Briefly, the EPD was applied to prepared pig skin and photos were taken before and after. Next, the wounds were treated overnight with a negative control foam and the EPD, respectively, and then photos were taken again. A comparative analysis of the photos showed that the EPD imparted more proteolytic activity upon the pig tissues than the negative control.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

What is claimed is:

1. A wound treatment system comprising a wound treatment apparatus and a wound dressing coupled to the wound treatment apparatus by a conduit, wherein the wound dressing is configured to be coupled to a wound of a patient, and wherein the apparatus comprises a vacuum source configured to apply negative pressure to the wound dressing via the conduit, wherein the wound dressing comprises an amine-functionalized polymer foam and a biologically active agent covalently attached to an amine group on the polymer foam.

2. The wound treatment system of claim 1, wherein the biologically active agent is attached to the foam through an adapter.

3. The wound treatment system of claim 1, wherein the biologically active agent is a polypeptide.

4. The wound treatment system of claim 3, wherein the polypeptide is selected from the group consisting of gelatin, collagen, albumin, an enzyme, growth factor, chemokine, cytokine, and a polypeptide that binds to any of them.

5. The wound treatment system of claim 4, wherein the polypeptide is an enzyme selected from a protease, hydrolase, lyase, ligase, isomerase, transferase, oxidase, reductase, oxidoreductase, synthase, polymerase, kinase, and phosphatase.

6. The wound treatment system of claim 1, comprising a polyurethane foam.

7. The wound treatment system of claim 6, comprising an open cell foam.

8. The wound treatment system of claim 1, wherein the amine-functionalized polymer foam comprises a polyurethane polymer copolymerized with an aminoglycoside.

9. The wound treatment system of claim 8, wherein the aminoglycoside comprises amikacin, arbekacin, gentamicin, kanamycin, netilmicin, paromomycin, rhodostreptomycin, streptomycin, tobramycin, framycetin, or apramycin.

10. The wound treatment system of claim 1, wherein the amine-functionalized polymer foam comprises a polyurethane polymer copolymerized with neomycin.

11. The wound treatment system of claim 1, wherein the biologically active agent is directly attached to the functionalized polymer foam.

12. The wound treatment system of claim 2, wherein the adapter is an amine to amine crosslinker.

13. The wound treatment system of claim 12, wherein the amine-to-amine crosslinker is selected from malondialdehyde, succinaldehyde, phthalaldehyde, glutaraldehyde, and glyoxal.

14. The wound treatment system of claim 13, wherein the crosslinker is glutaraldehyde.

15. The wound treatment system of claim 2, wherein the adapter is cleavable.

16. The wound treatment system of claim 7, wherein the material comprises a foam that is a reticulated open-celled foam.

17. The wound treatment system of claim 1, wherein the biologically active agent comprises a debridement enzyme.

18. The wound treatment system of claim 17, wherein the debridement enzyme comprises bromelain.

19. The wound treatment system of claim 17, wherein the debridement enzyme comprises papain.

20. The wound treatment system of claim 17, wherein the debridement enzyme comprises trypsin.

21. The wound treatment system of claim 17, wherein the debridement enzyme comprises collagenase.

22. The wound treatment system of claim 1, wherein the wound dressing comprises a modified wound insert and a drape, wherein the modified wound insert is configured to be positioned on the wound and the drape is configured to be coupled to skin of the patient adjacent the wound such that the drape covers the modified wound insert and the wound, and forms a space between the drape and the wound.

* * * * *

UNITED STATES PATENT AND TRADEMARK OFFICE
CERTIFICATE OF CORRECTION

PATENT NO. : 10,688,217 B2  
APPLICATION NO. : 15/830528  
DATED : June 23, 2020  
INVENTOR(S) : Hanson et al.

Page 1 of 2

It is certified that error appears in the above-identified patent and that said Letters Patent is hereby corrected as shown below:

On the Title Page

<u>Item (56), on Page 3, Column 2, Under (Other Publications)</u>
Line 2, delete "Philidelphia," and insert -- Philadelphia, --, therefor.

<u>Item (56), on Page 4, Column 1, Under (Other Publications)</u>
Line 19, delete "M. Morykwas," and insert -- M.J. Morykwas, --, therefor.

<u>Item (56), on Page 4, Column 2, Under (Other Publications)</u>
Line 3, delete "Hypermia" and insert -- Hyperemia --, therefor.

In the Specification

<u>Column 2</u>
Line 24, delete "Trimethyl silylmethanesulfonate," and insert
-- Trimethylsilylmethanesulfonate, --, therefor.
Line 25, delete "isothioronium" and insert -- isothiouronium --, therefor.
Line 37, delete "sisiomycin," and insert -- sisomicin, --, therefor.

<u>Column 3</u>
Line 43, delete "biolfilm" and insert -- biofilm --, therefor.

<u>Column 4</u>
Line 3, delete "devices" and insert -- devices. --, therefor.

<u>Column 5</u>
Line 49, delete "sisiomycin," and insert -- sisomicin, --, therefor.

<u>Column 6</u>
Line 17, delete "means=O;" and insert -- means =O; --, therefor.

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*

Line 23, delete "means=NH" and insert -- means =NH --, therefor.
Line 29, delete "means=S;" and insert -- means =S; --, therefor.

Column 7
Line 52, delete ""(Cn≤n)"" and insert -- "(C≤n)" --, therefor.

Column 11
Line 50, delete "(methyl carboxyl)," and insert -- (methylcarboxyl), --, therefor.

Column 12
Line 59, delete "monosacharides" and insert -- monosaccharides --, therefor.

Column 15
Line 21, delete "ortho-pthaldialdehyde;" and insert -- ortho-phthaldialdehyde; --, therefor.

Column 17
Line 66, delete "pthaldehyde," and insert -- phthalaldehyde, --, therefor.

Column 25
Line 22, delete "tetrammonium" and insert -- tetraammonium --, therefor.
Line 55, delete "enyzme" and insert -- enzyme --, therefor.

Column 32
Line 9, delete "and or" and insert -- and/or --, therefor.
Line 66, delete "and or" and insert -- and/or --, therefor.

Column 35
Line 15, delete "cytoxicity)." and insert -- cytotoxicity). --, therefor.